United States Patent
Hallinan et al.

(10) Patent No.: US 10,067,113 B2
(45) Date of Patent: Sep. 4, 2018

(54) ACETIC ACID PRODUCTION PROCESS

(71) Applicant: LyondellBasell Acetyls, LLC, Houston, TX (US)

(72) Inventors: Noel C. Hallinan, Loveland, OH (US); Brian A. Salisbury, Houston, TX (US); Daniel F. White, Houston, TX (US); David L. Ramage, Houston, TX (US)

(73) Assignee: LyondellBasell Acetyis, LLC, Houston, TX (US)

( * ) Notice: Subject to any disclaimer, the term of this patent is extended or adjusted under 35 U.S.C. 154(b) by 256 days.

(21) Appl. No.: 14/630,054

(22) Filed: Feb. 24, 2015

(65) Prior Publication Data

US 2015/0246866 A1    Sep. 3, 2015

Related U.S. Application Data

(60) Provisional application No. 61/946,269, filed on Feb. 28, 2014, provisional application No. 62/057,551, filed on Sep. 30, 2014.

(51) Int. Cl.
*C07C 51/12* (2006.01)
*C07C 53/08* (2006.01)
*G01N 33/20* (2006.01)

(52) U.S. Cl.
CPC ............. *G01N 33/20* (2013.01); *C07C 51/12* (2013.01)

(58) Field of Classification Search
CPC .......... C07C 51/12; C01C 53/08; G01N 33/20
See application file for complete search history.

(56) References Cited

U.S. PATENT DOCUMENTS

| | | | |
|---|---|---|---|
| 4,343,950 A | 8/1982 | Fiato et al. | |
| 5,214,203 A * | 5/1993 | Koyama | C07C 51/12 560/232 |
| 5,399,751 A | 3/1995 | Gertry et al. | |
| 5,817,869 A | 10/1998 | Hinnenkamp et al. | |

(Continued)

FOREIGN PATENT DOCUMENTS

| EP | 0132700 A1 | 2/1985 |
|---|---|---|
| WO | WO2005107945 A1 | 11/2005 |

OTHER PUBLICATIONS

Singapore Search Report and Written Opinion for Singapore Patent Application No. 11201606107T dated Dec. 27, 2016.

(Continued)

*Primary Examiner* — Robert J Eom

(57) ABSTRACT

Processes for producing acetic acid and determining corrosion therein are described herein. The processes generally include contacting methanol and carbon monoxide in the presence of a liquid reaction medium under carbonylation conditions sufficient to form acetic acid, wherein the liquid reaction medium includes: a carbonylation catalyst selected from rhodium catalysts, iridium catalysts and palladium catalysts; from 1 wt. % to 14 wt. % water; and one or more, in-situ generated derivatives of the one or more additives and combinations thereof; wherein the one or more additives are independently selected from non-benzoyl containing pentavalent phosphine oxides, compound mixtures of at least four phosphine oxides and pentavalent aryl or alkaryl phosphine oxides including one or more benzoyl groups; and recovering acetic acid from the process.

14 Claims, 7 Drawing Sheets

(56) References Cited

U.S. PATENT DOCUMENTS

| | | |
|---|---|---|
| 6,031,129 A | 2/2000 | Hinnenkamp et al. |
| 6,103,934 A | 8/2000 | Hallinan et al. |
| 6,686,500 B1 | 2/2004 | Watt |
| 2007/0298960 A1 | 12/2007 | Poole et al. |
| 2009/0326268 A1 | 12/2009 | Hanes et al. |
| 2012/0310009 A1 | 12/2012 | Hallinan et al. |
| 2013/0165688 A1 | 6/2013 | Le Berre et al. |

OTHER PUBLICATIONS

PCT International Search Report & Written Opinion dated Apr. 21, 2015 for PCT/US2015/017332.

D. V. Chavan et al., Journal of Chemical Technology and Biotechnology, 77, pp. 925-932, 2002.

M. A. Murphy et al., Journal of Organometallic Chemistry, 303, pp. 257-272, 1986.

A. Haynes et al., Journal of American Chemical Society, 126, pp. 2847-2861, 2004.

C. E. Hickey et al., Journal of the Chemical Society, Chemical Communications, pp. 1609-1611, 1984.

P. P. Sarmah et al., Journal of Molecular Catalysis A: Chemical 372, pp. 1-5, 2013.

\* cited by examiner

ACETIC ACID PRODUCTION PROCESS

CROSS-REFERENCE TO RELATED APPLICATIONS

This application claims the priority and benefit of U.S. Provisional Patent Application No. 61/946,269, filed Feb. 28, 2014, and U.S. Provisional Patent Application No. 62/057,551, filed Sep. 30, 2014, the content of which is incorporated herein by reference in their entirety.

STATEMENT REGARDING FEDERALLY SPONSORED RESEARCH OR DEVELOPMENT

Not applicable.

BACKGROUND

Field

The present disclosure generally relates to acetic acid production processes. In particular, embodiments contained herein relate to additives for acetic acid production processes.

Related Art

This section introduces information from the art that may be related to or provide context for some aspects of the techniques described herein and/or claimed below. This information is background facilitating a better understanding of that which is disclosed herein. This is a discussion of "related" art. That such art is related in no way implies that it is also "prior" art. The related art may or may not be prior art. The discussion is to be read in this light, and not as admissions of prior art.

Acetic acid may be commercially produced by methanol carbonylation. Methanol carbonylation processes often utilize a promoter, such as methyl iodide, in addition to carbonylation catalyst. A consequence of iodide promoted reactions is that, in addition to the added alkyl iodide, variable concentrations of in-situ generated hydrogen iodide may be present. Unfortunately, hydrogen iodide is highly corrosive. Continuous efforts have been directed towards reducing corrosion in acetic acid production processes.

Contained herein are embodiments directed to resolving, or at least reducing, one or all of the problems mentioned above.

SUMMARY

Embodiments disclosed herein include processes for producing acetic acid. In one or more embodiments, the processes generally include contacting methanol and carbon monoxide in the presence of a liquid reaction medium under carbonylation conditions sufficient to form acetic acid, wherein the liquid reaction medium includes: a carbonylation catalyst selected from rhodium catalysts, iridium catalysts and palladium catalysts; from 1 wt. % to 14 wt. % water; and an additive including a mixture of at least four phosphine oxides, wherein each phosphine oxide has the formula $OPX_3$, wherein O is oxygen, P is phosphorous and X is independently selected from $C_4$-$C_{18}$ alkyls, $C_4$-$C_{18}$ aryls, $C_4$-$C_{18}$ cyclic alkyls, $C_4$-$C_{18}$ cyclic aryls and combinations thereof and wherein each phosphine oxide has at least 15 carbon atoms; and recovering acetic acid from the process.

One or more embodiments include the process of the preceding paragraph, wherein the acetic acid is glacial acetic acid.

One or more embodiments include the process of any preceding paragraph, wherein the reaction medium includes from 1 wt. % to 10 wt. % water.

One or more embodiments include the process of any preceding paragraph, wherein the reaction medium includes from 1 wt. % to 6 wt. % water.

One or more embodiments include the process of any preceding paragraph, wherein the additive includes from 1 wt. % to 60 wt. % of each phosphine oxide based on the total weight of additive.

One or more embodiments include the process of any preceding paragraph, wherein the additive includes from 35 wt. % to 50 wt. % of each phosphine oxide based on the total weight of additive.

One or more embodiments include the process of any preceding paragraph, wherein the additive includes tri-n-octylphosphine oxide (TOPO), tri-n-hexylphosphine oxide (THPO), dihexylmonooctylphosphine oxide and dioctylmonohexylphosphine oxide.

One or more embodiments include the process of any preceding paragraph, wherein the additive includes from 12 wt. % to 16 wt. % tri-n-octylphosphine oxide (TOPO), from 8 wt. % to 16 wt. % tri-n-hexylphosphine oxide (THPO), from 28 wt. % to 32 wt. % dihexylmonooctylphosphine oxide and from 40 wt. % to 44 wt. % dioctylmonohexylphosphine oxide.

One or more embodiments include the process of any preceding paragraph, wherein the additive is a liquid at room temperature.

One or more embodiments include the process of any preceding paragraph, wherein the reaction medium includes from 0.1 mol/L to 1.8 mol/L additive.

One or more embodiments include the process of any preceding paragraph, wherein the reaction medium includes a molar ratio of additive to iodide of from 1:1 to 5:1.

One or more embodiments include the process of any preceding paragraph, wherein the carbonylation conditions include a temperature of from 150° C. to 250° C. and a pressure of from 200 psig (1379 kPa) to 2000 psig (13790 kPa).

One or more embodiments include the process of any preceding paragraph, wherein the process exhibits a corrosion rate that is at least 80% less than that of an identical process absent the additive.

One or more embodiments include the process of any preceding paragraph, wherein the contacting step takes place within a reaction zone and the process further includes introducing a second concentration of the additive into the process downstream of the reaction zone.

One or more embodiments include the process of any preceding paragraph, wherein the second concentration includes a molar ratio of additive to iodide of from 1:1 to 5:1.

One or more embodiments include the process of any preceding paragraph, wherein the second concentration includes a molar ratio of additive to iodide of from 2.5:1 to 3.5:1.

In one or more embodiments, the processes generally include contacting methanol and carbon monoxide in the presence of a liquid reaction medium under carbonylation conditions sufficient to form acetic acid, wherein the liquid reaction medium includes a carbonylation catalyst selected from rhodium catalysts, iridium catalysts and palladium catalysts; from 1 wt. % to 14 wt. % water; and an additive, in-situ generated additive derivatives and combinations thereof, wherein the additive includes a pentavalent aryl or alkaryl phosphine oxide comprising one or more benzoyl groups; and recovering acetic acid from the process.

One or more embodiments include the process of the preceding paragraph, wherein the acetic acid is glacial acetic acid.

One or more embodiments include the process of any preceding paragraph, wherein the reaction medium includes from 1 wt. % to 10 wt. % water.

One or more embodiments include the process of any preceding paragraph, wherein the reaction medium includes from 1 wt. % to 6 wt. % water.

One or more embodiments include the process of any preceding paragraph, wherein the additive is selected from bis(2,4,6-trimethylbenzoyl) phenyl phosphine oxide (BAPO), (2,4,6-trimethylbenzoyl)diphenyl phosphine oxide (TMDPO) and combinations thereof.

One or more embodiments include the process of any preceding paragraph, wherein the reaction medium includes from 0.01 mol/L to 0.5 mol/L additive.

One or more embodiments include the process of any preceding paragraph, wherein the reaction medium includes from 0.01 mol/L to less than 0.25 mol/L additive.

One or more embodiments include the process of any preceding paragraph, wherein the reaction medium includes a molar ratio of additive to iodide of from 0.01:1 to 5:1.

One or more embodiments include the process of any preceding paragraph, wherein the carbonylation conditions include a temperature of from 150° C. to 250° C. and a pressure of from 200 psig to 2000 psig.

One or more embodiments include the process of any preceding paragraph exhibiting a corrosion rate that is at least 80% less than that of an identical process absent the additive.

One or more embodiments include the process of any preceding paragraph further exhibiting a reaction rate that is from 25% lower to 25% higher than that of an identical process absent the additive.

In one or more embodiments, the processes generally include contacting methanol and carbon monoxide in the presence of a liquid reaction medium under carbonylation conditions sufficient to form acetic acid, wherein the liquid reaction medium includes a carbonylation catalyst including an iridium catalyst; from 1 wt. % to 14 wt. % water; and an additive, in-situ generated additive derivatives and combinations thereof, wherein the additive includes a pentavalent phosphine oxide having the formula $R_3P=O$, wherein each R is independently selected from substituted or unsubstituted alkyls, aryls, aralkyls and combinations thereof and recovering acetic acid from the process.

One or more embodiments include the process of the preceding paragraph, wherein the acetic acid is glacial acetic acid.

One or more embodiments include the process of any preceding paragraph, wherein the reaction medium includes from 1 wt. % to 10 wt. % water.

One or more embodiments include the process of any preceding paragraph, wherein the reaction medium includes from 1 wt. % to 6 wt. % water.

One or more embodiments include the process of any preceding paragraph, wherein the additive is selected from triethyl phosphine oxide, tributyl phosphine oxide, tripentyl phosphine oxide, diphenylmethyl phosphine oxide, triphenyl phosphine oxide and combinations thereof.

One or more embodiments include the process of any preceding paragraph, wherein the additive includes a phenyl group directly bonded to the phosphorous atom.

One or more embodiments include the process of any preceding paragraph, wherein the additive is selected from tributyl phosphine oxide, triphenyl phosphine oxide and combinations thereof.

One or more embodiments include the process of any preceding paragraph, wherein the reaction medium includes from 0.005 mol/L to 1.0 mol/L additive.

One or more embodiments include the process of any preceding paragraph, wherein the reaction medium includes from 0.01 mol/L to less than 0.25 mol/L additive.

One or more embodiments include the process of any preceding paragraph, wherein the reaction medium includes a molar ratio of additive to iodide of from 0.1:1 to 5:1.

One or more embodiments include the process of any preceding paragraph, wherein the carbonylation conditions include a temperature of from 150° C. to 250° C. and a pressure of from 200 psig (1379 kPa) to 2000 psig (13790 kPa).

One or more embodiments include the process of any preceding paragraph, exhibiting a corrosion rate that is at least 80% less than that of an identical process absent the additive.

One or more embodiments include the process of any preceding paragraph further exhibiting a reaction rate that is from 25% lower to 25% higher than that of an identical process absent the additive.

One or more embodiments include the process of any preceding paragraph, wherein the contacting step takes place within a reaction zone and the process further includes introducing a second concentration of the additive into the process downstream of the reaction zone.

One or more embodiments include the process of any preceding paragraph, wherein the second concentration includes a molar ratio of additive to iodide of from 0.01:1 to 5:1.

In one or more embodiments, the processes include contacting methanol and carbon monoxide in the presence of a liquid reaction medium under carbonylation conditions sufficient to form acetic acid, wherein the liquid reaction medium includes a carbonylation catalyst selected from rhodium catalysts, iridium catalysts and palladium catalysts; from 1 wt. % to 14 wt. % water; and from 0.001M to less than 0.20M additive, in-situ generated additive derivatives and combinations thereof, wherein the additive comprises a pentavalent phosphine oxide having the formula $R_3P=O$, wherein each R is independently selected from substituted or unsubstituted alkyls, aryls, aralkyls and combinations thereof; and recovering acetic acid from the process.

In one or more embodiments, the processes include contacting methanol and carbon monoxide in the presence of a liquid reaction medium under carbonylation conditions sufficient to form acetic acid, wherein the liquid reaction medium includes a carbonylation catalyst selected from rhodium catalysts, iridium catalysts and palladium catalysts; from 1 wt. % to 14 wt. % water; and an additive, in-situ generated additive derivatives and combinations thereof, wherein the additive comprises a pentavalent phosphine oxide having the formula $R_3P=O$, wherein each R is independently selected from substituted or unsubstituted alkyls, aryls, aralkyls and combinations thereof, wherein the reaction medium includes a molar ratio of additive to iodide of from 0.01:1 to 5:1; and recovering acetic acid from the process.

In one or more embodiments, the processes generally include contacting methanol and carbon monoxide in the presence of a liquid reaction medium under carbonylation conditions sufficient to form acetic acid, wherein the liquid reaction medium includes: a carbonylation catalyst selected from rhodium catalysts, iridium catalysts and palladium catalysts; from 1 wt. % to 14 wt. % water; and an additive package including at least two additives, in-situ generated derivatives of the at least two additives and combinations thereof; wherein the at least two additives are independently selected from non-benzoyl containing pentavalent phosphine oxides, compound mixtures of at least four phosphine oxides and pentavalent aryl or alkaryl phosphine oxides including one or more benzoyl groups; wherein the non-benzoyl containing pentavalent phosphine oxides have the formula $R_3P=O$, wherein each R is independently selected from substituted or unsubstituted alkyls, aryls, aralkyls and combinations thereof; and wherein each phosphine oxide of the compound mixtures has the formula $OPX_3$, wherein O is oxygen, P is phosphorous and X is independently selected from $C_4$-$C_{18}$ alkyls, $C_4$-$C_{18}$ aryls, $C_4$-$C_{18}$ cyclic alkyls, $C_4$-$C_{18}$ cyclic aryls and combinations thereof and wherein each phosphine oxide has at least 15 carbon atoms; and recovering acetic acid from the process.

One or more embodiments include the process of the preceding paragraph, wherein the acetic acid is glacial acetic acid.

One or more embodiments include the process of any preceding paragraph, wherein the reaction medium includes from 1 wt. % to 10 wt. % water.

One or more embodiments include the process of any preceding paragraph, wherein the reaction medium includes from 1 wt. % to 6 wt. % water.

One or more embodiments include the process of any preceding paragraph, wherein the reaction medium includes an additive package concentration of from 0.005 mol/L to 2.0 mol/L.

One or more embodiments include the process of any preceding paragraph, wherein the reaction medium comprises a molar ratio of additive package to iodide of from 0.005:1 to 5:1.

One or more embodiments include the process of any preceding paragraph, wherein the carbonylation conditions include a temperature of from 150° C. to 250° C. and a pressure of from 200 psig (1379 kPa) to 2000 psig (13790 kPa).

One or more embodiments include the process of any preceding paragraph exhibiting a corrosion rate that is at least 80% less than that of an identical process absent the additive package.

One or more embodiments include the process of any preceding paragraph further exhibiting a reaction rate that is from 25% lower to 25% higher than that of an identical process absent the additive package.

One or more embodiments include the process of any preceding paragraph, wherein the compound mixture includes from 1 wt. % to 60 wt. % of each phosphine oxide based on the total weight of compound mixture.

One or more embodiments include the process of any preceding paragraph, wherein the compound mixture includes from 35 wt. % to 50 wt. % of each phosphine oxide based on the total weight of compound mixture.

One or more embodiments include the process of any preceding paragraph, wherein the compound mixture includes tri-n-octylphosphine oxide (TOPO), tri-n-hexylphosphine oxide (THPO), dihexylmonooctylphosphine oxide and dioctylmonohexylphosphine oxide.

One or more embodiments include the process of any preceding paragraph, wherein the compound mixture includes from 12 wt. % to 16 wt. % tri-n-octylphosphine oxide (TOPO), from 8 wt. % to 16 wt. % tri-n-hexylphosphine oxide (THPO), from 28 wt. % to 32 wt. % dihexylmonooctylphosphine oxide and from 40 wt. % to 44 wt. % dioctylmonohexylphosphine oxide.

One or more embodiments include the process of any preceding paragraph, wherein the compound mixture is a liquid at room temperature.

One or more embodiments include the process of any preceding paragraph, wherein the pentavalent aryl or alkaryl phosphine oxides including one or more benzoyl groups are selected from bis(2,4,6-trimethylbenzoyl) phenyl phosphine oxide (BAPO), (2,4,6-trimethylbenzoyl) diphenyl phosphine oxide (TMDPO) and combinations thereof.

One or more embodiments include the process of any preceding paragraph, wherein the non-benzoyl containing pentavalent phosphine oxides are selected from triethyl phosphine oxide, tributyl phosphine oxide, tripentyl phosphine oxide, diphenylmethyl phosphine oxide, triphenyl phosphine oxide and combinations thereof.

One or more embodiments include the process of any preceding paragraph, wherein the non-benzoyl containing pentavalent phosphine oxides include a phenyl group directly bonded to the phosphorous atom.

One or more embodiments include the process of any preceding paragraph, wherein the non-benzoyl containing pentavalent phosphine oxides are selected from tributyl phosphine oxide, triphenyl phosphine oxide and combinations thereof.

One or more embodiments include the process of any preceding paragraph, wherein the additive package includes a primary additive and a secondary additive.

One or more embodiments include the process of any preceding paragraph, wherein the primary additive includes the compound mixture.

One or more embodiments include the process of any preceding paragraph, wherein the secondary additive includes the pentavalent aryl or alkaryl phosphine oxides including one or more benzoyl groups.

One or more embodiments include the process of any preceding paragraph, wherein the secondary additive includes the pentavalent phosphine oxides.

One or more embodiments include the process of any preceding paragraph, wherein the secondary additive is directly mixed with the primary additive to form the additive package.

One or more embodiments include the process of any preceding paragraph, wherein the primary additive includes the pentavalent aryl or alkaryl phosphine oxides comprising one or more benzoyl groups.

One or more embodiments include the process of any preceding paragraph, wherein the secondary additive includes the non-benzoyl containing pentavalent phosphine oxide.

One or more embodiments include the process of any preceding paragraph, wherein the primary and secondary additives are selected from the pentavalent aryl or alkaryl phosphine oxides including one or more benzoyl groups.

One or more embodiments include the process of any preceding paragraph, wherein the additive package includes essentially equal concentrations of each of the at least two additives.

One or more embodiments include the process of any preceding paragraph, wherein the additive package further includes a third additive selected from the non-benzoyl containing pentavalent phosphine oxides, compound mixtures of at least four phosphine oxides and pentavalent aryl or alkaryl phosphine oxides comprising one or more benzoyl groups.

One or more embodiments include processes for determining corrosion. The processes generally include providing a batch reactor; disposing a solution including components of a liquid reaction medium of a target reaction within the batch reactor, wherein the solution is absent catalyst and feedstock for the target reaction; operating the batch reactor at reaction conditions simulating the target reaction for a reaction time sufficient to determine the corrosion of the batch reactor; retrieving the solution from the batch reactor; and analyzing the solution for a metal concentration therein.

One or more embodiments include the process of the preceding paragraph, wherein the one or more phosphine oxide additives are selected from non-benzoyl containing pentavalent phosphine oxides, compound mixtures of at least four phosphine oxides and pentavalent aryl or alkaryl phosphine oxides comprising one or more benzoyl groups.

One or more embodiments include the process of any preceding paragraph, wherein the target reaction is an acetic acid production process.

One or more embodiments include the process of any preceding paragraph, wherein the solution is analyzed via inductively coupled plasma (ICP).

One or more embodiments include the process of any preceding paragraph, wherein the reaction conditions include a temperature of from 150° C. to 220° C. and a pressure of 100 psi to 1000 psi.

One or more embodiments include the process of any preceding paragraph, wherein the reaction time includes from 0.5 hours to 3.5 hours.

One or more embodiments include the process of any preceding paragraph, wherein the reaction time includes a time of up to 1 hour.

The above paragraphs present a simplified summary of the presently disclosed subject matter in order to provide a basic understanding of some aspects thereof. The summary is not an exhaustive overview, nor is it intended to identify key or critical elements to delineate the scope of the subject matter claimed below. Its sole purpose is to present some concepts in a simplified form as a prelude to the more detailed description set forth below.

BRIEF DESCRIPTION OF THE DRAWINGS

The claimed subject matter may be understood by reference to the following description taken in conjunction with the accompanying drawings, in which like reference numerals identify like elements, and in which:

Figure 1:
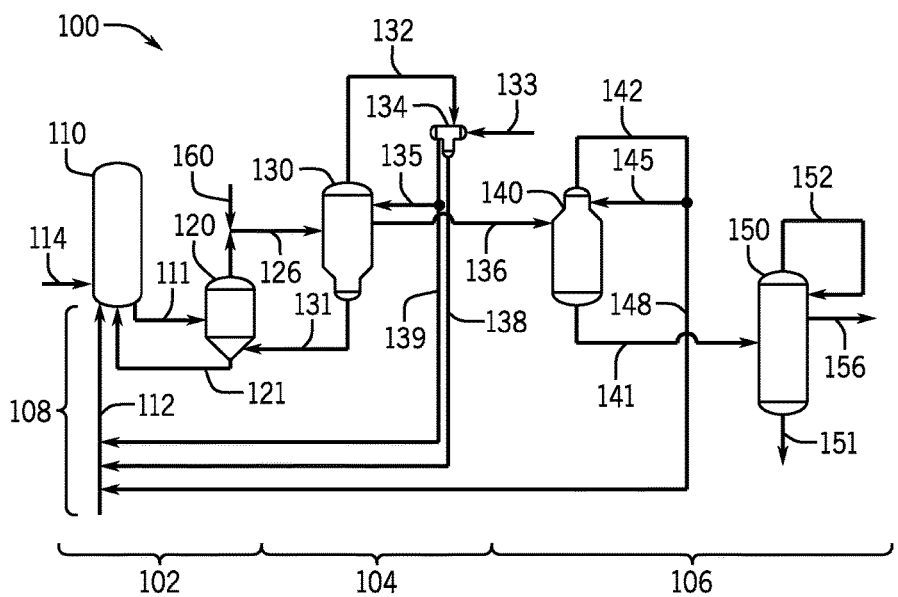
FIG. 1 illustrates a schematic of one or more embodiments of the disclosed process.

While the claimed subject matter is susceptible to various modifications and alternative forms, the drawings illustrate specific embodiments herein described in detail by way of example. It should be understood, however, that the description herein of specific embodiments is not intended to limit the claimed subject matter to the particular forms disclosed, but on the contrary, the intention is to cover all modifications, equivalents, and alternatives falling within the spirit and scope as defined by the appended claims.

DETAILED DESCRIPTION

Illustrative embodiments of the subject matter claimed below will now be disclosed. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

In the description below, unless otherwise specified, all compounds described herein may be substituted or unsubstituted and the listing of compounds includes derivatives thereof. Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations.

Embodiments described herein generally include processes for producing carboxylic acids. It will be realized that while specific embodiments herein may refer to acetic acid production processes, it is to be understood by one skilled in the art that such embodiments may be utilized in other carboxylic acid production processes. Furthermore, one or more specific embodiments include production of glacial acetic acid (which is encompassed by the term "acetic acid" as referenced herein). Glacial acetic acid refers to acetic acid that is generally undiluted (includes a water concentration at most in the parts per million range).

The acetic acid production processes generally include carbonylation processes. For example (and for purposes of discussion herein), the acetic acid production processes may include the carbonylation of methanol or its derivatives to produce acetic acid. As referenced previously herein, the embodiments described herein are also applicable to the carbonylation of higher homologues of methanol, such as ethanol, butanol and pentanol, for example, to produce acids which are higher homologues of acetic acid. The adaptation of the embodiments to such systems will be readily apparent to the artisan given the following discussion.

Carbonylation processes generally include reacting an alcohol, such as methanol, with carbon monoxide in a liquid reaction medium under carbonylation conditions sufficient to form acetic acid and recovering the formed acetic acid from the process.

The reaction medium generally includes a carbonylation catalyst. Suitable carbonylation catalysts include, but are not limited to, rhodium catalysts, iridium catalysts and palladium catalysts. Suitable rhodium catalysts include rhodium metal and rhodium compounds selected from rhodium salts, rhodium oxides, rhodium acetates, organo-rhodium compounds, coordination compounds of rhodium and mixtures thereof, for example. (See, U.S. Pat. No. 5,817,869, which is incorporated in its entirety herein.) Suitable iridium catalysts include iridium metal and iridium compounds selected from acetates, oxalates, acetoacetates and mixtures thereof, for example. (See, U.S. Pat. No. 5,932,764, which is incorporated in its entirety herein.)

The concentration of carbonylation catalyst utilized in the reaction medium may be from 1 mmol to 100 mmol, or from 2 mmol to 5 mmol, or at least 7.5 mmol, or from 2 mmol to 75 mmol, or from 5 mmol to 50 mmol, or from 7.5 mmol to 25 mmol of catalyst per liter of reaction medium, for example.

In one or more embodiments, the carbonylation catalyst is utilized with a co-catalyst. The co-catalyst may be selected from metal and metal compounds selected from osmium, rhenium, ruthenium, cadmium, mercury, zinc, gallium, indium, tungsten and mixtures thereof.

In one or more embodiments, the reaction medium includes from 2 wt. % to 14 wt. %, or 10 wt. % or less, or 8 wt. % or less, or 6 wt. % or less, or from 1 wt. % to 5 wt. %, or from 4 wt. % to 8 wt. % water based on the total weight of the reaction medium, for example. However, utilization of iodide promoter within the reaction medium can result in in-situ generation of hydrogen iodide. Unfortunately, hydrogen iodide is highly corrosive and therefore is undesirable in the carbonylation process.

The reaction medium may further include a variety of additives or other components (i.e., components other than the alcohol, carbon monoxide and carbonylation catalyst). The introduction of such additives to the reaction medium can be via any method known in the art. For example, each of the additives may be, either independently or as a mixture, introduced directly to the reaction medium. Alternatively, one or more of the additives may be generated in-situ, for example.

In the embodiments described herein, the additives include one or more phosphine oxides as described herein. It should be understood that the effect of the additives described herein may range from those that allow substantially improved catalyst stabilization and substantially improved corrosion inhibition, to those that principally allow substantially improved catalyst stabilization and to those that principally allow improved corrosion inhibition, for example. Such improvements (decreased corrosion &/or improved catalyst stability) are possible while achieving acceptable, if not exceptional, rates of reaction.

A variety of methods of determining corrosion/corrosion rates exist. However, embodiments described herein refer to corrosion rates that are determined by a method not previously known in the art. Prior methods generally had difficulty comparing corrosion amounts between various runs or from one system to another. However, one or more embodiments include determining a corrosion rate for a process that is comparable regardless of run or system. In one or more embodiments, the corrosion determination includes a batch reactor method in which runs are dedicated to measuring a single variable, corrosion. In such a method, no catalyst or methyl feed stock are present. Without catalyst or feedstock, the corrosion determination is made under steady state conditions and corrosion rates of the internal surface of the reactor can be directly correlated to the starting solution chemical composition.

The method of determining corrosion generally includes providing a batch reactor; disposing a solution comprising the components of the liquid reaction medium (absent the carbonylation catalyst, alcohol and methanol); operating the batch reactor at reaction conditions for a time of from 0.5 hours to 5 hours, or from 0.75 hours to 3.5 hours, or of up to 1 hour; withdrawing the solution from the batch reactor; and analyzing the solution for metal concentration therein. In one or more embodiments, the solution includes water, optionally one or more additives, hydrogen iodide (HI) and/or acetic acid. The concentration of the individual components of the solution is selected to simulate the liquid reaction medium described herein. The solution may be analyzed by a variety of methods, including inductively coupled plasma ICP, for example The batch reactor is generally formed of any metal that is resistant to the corrosive effects of the process described herein. However, it is also recognized in the art that such corrosion resistance may not be 100% effective. In one or more specific embodiments, the batch reactor is selected from a Hastalloy C276, Hastalloy B and Hastalloy B3 batch reactor. In one or more embodiments, the batch reactor has an internal surface that is at least 1 or up to 5, or up to 3 orders of magnitude greater than a metal coupon, such as that used in experimental descriptions below.

The reaction conditions model those of the process targeted for corrosion measurements. For example, when modeling the corrosion in an acetic acid production process, the reaction conditions will generally simulate those of the acetic acid production process. In one or more embodiments, the reaction conditions include a temperature of from 100° C. to 300° C., or from 150° C. to 220° C., and a pressure of from 100 psi (690 kPa) to 1000 psi (6900 kPa), or from 125 psi (862 kPa) to 875 psi (6033 kPa), or from 150 psi (1034 kPa) to 800 psi (5515 kPa), for example.

In one or more embodiments, the additives include a compound mixture of at least four phosphine oxides, where each phosphine oxide has the formula $OPX_3$, wherein O is oxygen, P is phosphorous and X is independently selected from $C_4$-$C_{18}$ alkyls, $C_4$-$C_{18}$ aryls, $C_4$-$C_{18}$ cyclic alkyls, $C_4$-$C_{18}$ cyclic aryls and combinations thereof. Each phosphine oxide has at least 15, or at least 18 total carbon atoms.

Examples of suitable phosphine oxides for use in the compound mixture include, but are not limited to, tri-n-hexylphosphine oxide (THPO), tri-n-octylphosphine oxide (TOPO), tris(2,4,4-trimethylpentyl)-phosphine oxide, tricyclohexylphosphine oxide, tri-n-dodecylphosphine oxide, tri-n-octadecylphosphine oxide, tris(2-ethylhexyl)phosphine oxide, di-n-octylethylphosphine oxide, di-n-hexylisobutylphosphine oxide, octyldiisobutylphosphine oxide, tribenzylphosphine oxide, di-n-hexylbenzylphosphine oxide, di-n-octylbenzylphosphine oxide, 9-octyl-9-phosphabicyclo[3.3.1]nonane-9-oxide, dihexylmonooctylphosphine oxide, dioctylmonohexylphosphine oxide, dihexylmonodecylphosphine oxide, didecylmonohexylphosphine oxide, dioctylmonodecylphosphine oxide, didecylmonooctylphosphine oxide, and dihexylmonobutylphosphine oxide and the like.

The compound mixture includes from 1 wt % to 60 wt. %, or from 35 wt. % to 50 wt. % of each phosphine oxide based on the total weight of compound mixture. In one or more specific, non-limiting embodiments, the compound mixture includes TOPO, THPO, dihexylmonooctylphosphine oxide and dioctylmonohexylphosphine oxide. For example, the compound mixture may include from 40 wt. % to 44 wt % dioctylmonohexylphosphine oxide, from 28 wt. % to 32 wt. % dihexylmonooctylphosphine oxide, from 8 wt. % to 16 wt. % THPO and from 12 wt. % to 16 wt. % TOPO, for example.

In one or more embodiments, the compound mixture exhibits a melting point of less than 20° C., or less than 10° C., or less than 0° C., for example.

In one or more specific embodiments, the compound mixture is Cyanex®923, commercially available from Cytec Corporation.

Each individual component of the compound mixture is solid while the mixture is liquid at room temperature. As used herein, "room temperature" means that a temperature difference of a few degrees does not matter to the phenomenon under investigation, such as a preparation method. In some environments, room temperature may include a temperature of from about 20° C. to about 28° C. (68° F. to 82° F.), while in other environments, room temperature may include a temperature of from about 50° F. (10° C.) to about 90° F. (32° C.), for example. However, room temperature measurements generally do not include close monitoring of the temperature of the process and therefore such a recitation does not intend to bind the embodiments described herein to any predetermined temperature range.

Mixtures and methods of forming such compound mixtures are described in U.S. Pat. No. 4,909,939, which is incorporated in its entirety herein.

The concentration of compound mixture in the reaction medium should be sufficient to maintain the activity and/or stability of the carbonylation catalyst. For example, the concentration of compound mixture in the reaction medium may be from 0.05 mol/L to 1.8 mol/L, or from 0.1 mol/L to 1.8 mol/L, or from 0.2 mol/L to 1.8 mol/L, or from 0.25 mol/L to 1.5 mol/L, or from 0.5 mol/L to 1.0 mol/L of reaction medium (measured at cold degassed conditions), for example. Alternatively, the compound mixture concentration may be determined depending on the HI content. For example, the molar ratio of additive to iodide may be from 1:1 to 5:1, or from 2:1 to 4:1, or from 2.5:1 to 3.5:1.

It has been observed that the use of the specific compound mixture described herein inhibits corrosion at an unexpected rate. For example, the process may exhibit corrosion at a rate (measured as described in the examples that follow herein) that is at least 50%, or at least 60%, or at least 70%, or at least 75%, or at least 80%, or at least 85%, or at least 90%, or at least 95% less than that of an identical process absent the additive as disclosed herein.

In one or more embodiments, the additives include a pentavalent aryl or alkaryl phosphine oxide containing one or more benzoyl groups (i.e., benzoyl containing phosphine oxide). These benzoyl groups may be substituted or unsubstituted, for example. It should be understood that the effect of additives may range from those that allow substantially improved catalyst stabilization and substantially improved corrosion inhibition, to those that principally allow substantially improved catalyst stabilization and to those that principally allow improved corrosion inhibition, for example.

In one or more embodiments, the benzoyl containing phosphine oxide may be selected from bis(2,4,6-trimethylbenzoyl) phenyl phosphine oxide (BAPO), (2,4,6-trimethylbenzoyl)diphenyl phosphine oxide (TMDPO) or combinations thereof, for example. While the one or more additives are introduced to the reaction medium, it should be noted that the additives may react with components within the reaction medium and the additives, the in-situ generated components or combinations thereof may function as a corrosion inhibitor. Accordingly, the reaction medium may include the components introduced thereto (e.g., the benzoyl group containing phosphine oxide), any in-situ generated related components due to reaction, such as hydrolysis, and combinations thereof.

The concentration of benzoyl containing phosphine oxide introduced into the reaction medium should be sufficient to maintain the activity, the stability or a combination thereof of the carbonylation catalyst. For example, the additive concentration introduced into the reaction medium may be from 0.005M to 2.0M, or from 0.01M to 0.5M, or from 0.25M to 0.5M, or from 0.1M to 0.25M, for example. Alternatively, the additive concentration may be determined depending on the HI content. For example, the molar ratio of additive to iodide may be from 0.01:1 to 5:1, or from 0.25:1 to 4:1, or from 0.5:1 to 3.5:1. While referenced herein as a molar ratio of additive to iodide, it is to be understood that only ionizable iodides, principally HI and to a lesser extent corrosion metal iodides, increase corrosion rate and any reference to iodides in relation thereof and impact on corrosion do not include alkyl iodides.

It has been observed that the use of the specific additives described herein inhibit corrosion at an unexpected rate. For example, the process may exhibit corrosion at a rate (i.e., at a "corrosion rate" measured as described in the examples that follow herein and defined as coupon weight % loss/48 hours) that is at least 50%, or at least 60%, or at least 70%, or at least 75%, or at least 80%, or at least 85%, or at least 90%, or at least 95% less than that of an identical process absent the specific additives as disclosed herein. It has further been observed that the process may exhibit corrosion of 15% or less, or 10% or less, or 5% or less, or 2% or less. In fact, corrosion rates of 0% may be possible with the embodiments described herein. Furthermore, it has been observed that such corrosion rate can occur at a benzoyl containing phosphine oxide concentration lower than 0.01M, for example.

It has further been observed that such decreased corrosion can be obtained without a significantly decreased rate of reaction. For example, such decreased corrosion rates may be observed with less than 25%, or less than 20%, or less than 15%, or less than 10%, or less than 5% decrease in reaction rate. However, it is contemplated that rather than limited decreases in reaction rates, no decrease in reaction rate or an actual increase in reaction rate may be obverserved with the embodiments described herein. For example, the decreased corrosion rates may be observed with from a 25% decrease in reaction rate to a 25% increase in reaction rate. Such reaction rates can be observed with all carbonylation catalysts described herein, but are particularly relevant with Ir based catalysts, which tend to exhibit rapid reaction rate reductions upon contact with phosphine oxide. However, embodiments described herein may be capable of use in Ir based catalyst systems with no observable decrease (and potentially an increase as described above) in reaction rate.

In one or more embodiments described herein, the additives include a pentavalent phosphine oxide (for ease of reference herein and to distinguish from prior referenced benzoyl containing pentavalent phosphine oxides, these compounds will be referred to herein as non-benzoyl group containing pentavalent phosphine oxides). The non-benzoyl containing pentavalent phosphine oxides generally have the formula $R_3P=O$, wherein each R is independently selected from substituted or unsubstituted alkyls, aryls, aralkyls and combinations thereof. For example, each R may be independently selected from methyl, ethyl, propyl, isopropyl, butyl, isobutyl, t-butyl, amyl, pentyl, hexyl, octyl, phenyl, naphthyl and combinations thereof, for example. When substituted, each substituent on each R group may be independently selected from those defined herein above for R, as well as halogens, hydroxyl groups, nitrogen groups, amino groups and combinations thereof, for example. Specific, non-limiting embodiments include triethyl phosphine oxide, tributyl phosphine oxide, tripentyl phosphine oxide, diphenylmethyl phosphine oxide, triphenyl phosphine oxide and combinations thereof, for example. In one or more specific embodiments, the non-benzoyl containing pentavalent phosphine oxides include a phenyl group directly bonded to the phosphorous atom. In one or more specific embodiments, the non-benzoyl containing pentavalent phosphine oxides are selected from tri-butyl phosphine oxide (TBPO), tri-phenyl phosphine oxide (TPPO) and combinations thereof.

The concentration of non-benzoyl containing pentavalent phosphine oxide in the reaction medium should be sufficient to maintain the activity, the stability or a combination thereof of the carbonylation catalyst. For example, the non-benzoyl containing pentavalent phosphine oxide concentration in the reaction medium may be from 0.005M to 2.0M, or from 0.01M to 0.5M, or from 0.25M to 0.51M, or from 0.1M to 0.25M, for example. Alternatively, the non-benzoyl containing pentavalent phosphine oxide concentration may be determined depending on the HI content. For example, the molar ratio of non-benzoyl containing pentavalent phosphine oxide to iodide may be from 0.005:1 to 5:1, or from 0.01:1 to 4:1, or from 0.25:1 to 3.5:1.

It has been observed that the use of the specific additives described herein inhibits corrosion at an unexpected rate. For example, the process may exhibit corrosion at a rate (measured as described in the examples that follow herein) that is at least 50%, or at least 60%, or at least 70%, or at least 75%, or at least 80%, or at least 85%, or at least 90%, or at least 95% less than that of an identical process absent the additive as disclosed herein. It has further been observed that the process may exhibit corrosion of 15% or less, or 10% or less, or 5% or less, or 2% or less. In fact, corrosion rates of 0% may be possible with the embodiments described herein. Furthermore, it has been observed that such corrosion rate can occur at a additive concentration lower than 0.01M, for example.

It has further been observed that such decreased corrosion can be obtained without a significantly decreased rate of reaction. For example, such decreased corrosion rates may be observed with less than 25%, or less than 20%, or less than 15%, or less than 10%, or less than 5% decrease in reaction rate. Such decrease in reaction rate can be observed with all carbonylation catalysts described herein, but are particularly relevant with Ir based catalysts, which tend to exhibit rapid reaction rate reductions upon contact with phosphine oxide. However, embodiments described herein may be capable of use in Ir based catalyst systems with no observable decrease in reaction rate.

Further, one or more embodiments include introducing the pentavalent phosphine oxide to the acetic acid production process downstream of the carbonylation reaction. As used herein, the expression "downstream" refers to all processing steps which are taken in subsequent stages of the process. Such introduction may be in addition to addition of the pentavalent phosphine oxide to the reaction medium (i.e., a second concentration of additive) or as an alternative to addition to the reaction medium. Such use of the pentavalent phosphine oxide results in reduced corrosion to equipment downstream from the carbonylation reaction compared to identical processes absent the second concentration of additive, for example.

The concentration of pentavalent phosphine oxide introduced to the acetic acid production process downstream of the carbonylation reaction (i.e., the second concentration) is generally not critical so long as the pentavalent phosphine oxide is provided in an effective amount. An effective amount in this context is the amount of pentavalent phosphine oxide which is capable of scavenging at least a portion of the HI present within a designated portion of the acetic acid production process.

In one or more embodiments, the second concentration may be adjusted depending on the HI content. For example, a downstream iodide concentration of 1000 ppm may utilize a concentration of from about 2000 ppm to about 4000 ppm of pentavalent phosphine oxide to remove from 50% to 100% iodide from the target stream. Accordingly, the molar ratio of pentavalent phosphine oxide to iodide concentration may be from 1:1 to 5:1, or from 2:1 to 4:1, or from 2.5:1 to 3.5:1, for example.

In one or more embodiments described herein, the additive includes an additive package. The additive package includes at least two additives. While discussed with reference to the at least two additives, it is contemplated and within the description herein that the additive package may further include additional additives. The at least two additives may be in the form of a mixture (with or without additional additives therein) or they may be introduced to the reaction medium separately. However, it is contemplated within the embodiments described herein that at least a portion of the at least two additives contact the reaction medium simultaneously. Those skilled in the art of acetic acid processing via methanol carbonylation will appreciate that corrosion is a relatively slow process and that the order of addition of the at least two additives is not of great importance so long as there is not a long period between the separate additions. For optimal corrosion inhibition, the additives should be added nearly simultaneously, where this term refers to up to about 2 weeks between the separate additions. Furthermore, it is contemplated that the concentration of one or more of the additives within the additive package may be introduced to the reaction medium at various intervals (i.e., dynamic introduction). In such embodiments, it is contemplated that the concentration of the additive will fall within those ranges described herein at any given time during the reaction, despite the possibility of a concentration fluctuation.

It should be understood that the effect of additives may range from those that allow substantially improved catalyst stabilization and substantially improved corrosion inhibition, to those that principally allow substantially improved catalyst stabilization and to those that principally allow improved corrosion inhibition, for example. Such improvements (decreased corrosion &/or improved catalyst stability) are possible while achieving acceptable, if not exceptional, rates of reaction.

The at least two additives may be independently selected from the non benzoyl containing pentavalent phosphine oxides, the compound mixture of at least four phosphine oxides, and the pentavalent aryl or alkaryl phosphine oxides containing one or more benzoyl groups (i.e., benzoyl containing pentavalent phosphine oxides).

While the at least two additives are introduced to the reaction medium, it should be noted that the additives may react with components within the reaction medium and the additives, the in-situ generated components or combinations thereof may function as a corrosion inhibitor. Accordingly, the reaction medium may include the components introduced thereto (e.g., the at least two additives), any in-situ generated related components due to reaction, such as hydrolysis, and combinations thereof.

The concentration of the additive package in the reaction medium may be sufficient to maintain the activity, the stability or a combination thereof of the carbonylation catalyst. For example, the total concentration in the reaction medium may be from 0.005M to 2.0M, or from 0.01M to 0.5M, or from 0.25M to 0.5M, or from 0.1M to 0.25M, for example. Alternatively, the total concentration may be determined depending on the HI content. For example, the molar ratio of the at least two additives to iodide may be from 0.005:1 to 5:1, or from 0.01:1 to 4:1, or from 0.25:1 to 3.5:1. While referenced herein as a molar ratio of additive to iodide, it is to be understood that only ionizable iodides, principally HI and to a lesser extent corrosion metal iodides, increase corrosion rate and any reference to iodides in relation thereof and impact on corrosion do not include alkyl iodides.

In one or more embodiments, the additive package (i.e., the at least two additives) includes a primary additive and a secondary additive. In such embodiments, the additive package includes greater than 50 mol. %, or at least 60 mol. %, or at least 70 mol. %, or at least 80 mol. %, or at least 90 mol. %, or at least 95 mol. %, or at least 97 mol. %, or at least 98 mol. %, or at least 99 mol. % primary additive, for example. In alternative embodiments, the at least two additives are utilized in essentially equal amounts.

In one or more specific embodiments, the primary additive is the compound mixture of at least 4 phosphine oxides and the secondary additive is the benzoyl containing pentavalent phosphine oxide. For example, the primary additive may be Cyanex®923 and the secondary additive may be BAPO. Alternatively, the primary additive may be Cyanex®923 and the secondary additive may be TMDPO. It is contemplated that in yet other embodiments, the primary additive may be Cyanex®923, and the secondary additive may include both BAPO and TMDPO. Alternatively, the primary additive may be the benzoyl containing pentavalent phosphine oxide while the secondary additive may be the compound mixture. It is further contemplated that each of the additives is utilized in essentially equal concentrations and therefore there is no primary and no secondary additive but rather two additives.

As discussed previously herein, the individual components of the additive package (i.e., the at least two additives) can be pre-mixed prior to introduction into the reaction medium or may be introduced to the reaction medium separately. For example, when utilizing the compound mixture as primary or secondary additive, it is contemplated that the compound mixture may be introduced into the reaction mixture as a liquid, while the other additive(s) may be introduced into the reaction mixture as solids in appropriate quantities to achieve the desired molar ratios. However, again when utilizing the compound mixture as either primary or secondary additive, one or more specific embodiments include dissolving the alternative of the at least two additives directly in the compound mixture to form an additive mixture. Such embodiments can provide for tighter control of target molar ratios and thereby improved process control.

The dissolution may occur via methods including adding excess of each additive and heating the resulting slurry until solubilized. While it may be contemplated that one or more components of the additive mixture may precipitate from the solution upon cooling to room temperature, the mixture will re-solubilize upon re-heating, even absent mixing and therefore can be utilized directly into acetic acid production processes.

In one or more specific embodiments, the primary additive is the benzoyl containing pentavalent phosphine oxide and the secondary additive is the non-benzoyl containing pentavalent phosphine oxide. For example, the primary additive may be BAPO and the secondary additive may be TBPO. Alternatively, the primary additive may be the non-benzoyl containing pentavalent phosphine oxide while the secondary additive may be the benzoyl containing pentavalent phosphine oxide.

In one or more specific embodiments, the primary additive is the compound mixture of at least 4 phosphine oxides and the secondary additive is the non-benzoyl containing pentavalent phosphine oxide. For example, the primary additive may be Cyanex®923 and the secondary additive may be TPPO. Alternatively, the primary additive may be Cyanex®923 and the secondary additive may be TBPO. It is contemplated that in yet other embodiments, the primary additive may be Cyanex®923, and the secondary additive may include both TPPO and TBPO. Alternatively, the primary additive may be the non-benzoyl containing pentavalent phosphine oxide while the secondary additive may be the compound mixture. It is further contemplated that each of the additives is utilized in essentially equal concentrations and therefore there is no primary and no secondary additive but rather two additives.

In one or more specific embodiments, the primary additive and the secondary additives are benzoyl containing pentavalent phosphine oxides. For example, the primary additive may be TMDPO and the secondary additive may be BAPO. Alternatively, the primary additive may be BAPO and the secondary additive may be TMDPO. It is further contemplated that each of the additives is utilized in essentially equal concentrations and therefore there is no primary and no secondary additive but rather two additives.

It has been observed that the use of the specific additives described herein inhibits corrosion at an unexpected rate. For example, the process may exhibit corrosion at a rate (measured as described in the examples that follow herein) that is at least 50%, or at least 60%, or at least 70%, or at least 75%, or at least 80%, or at least 85%, or at least 90%, or at least 95% less than that of an identical process absent the additive as disclosed herein. It has further been observed that the process may exhibit corrosion of 15% or less, or 10% or less, or 5% or less, or 2% or less. In fact, corrosion rates of 0% may be possible with the embodiments described herein.

It has further been observed that one or more embodiments utilizing at least two additives (i.e., the additive package) may provide an order of magnitude further decrease in corrosion rate than utilizing either of the additives alone. Furthermore, it has been observed that such corrosion rate can occur at a secondary additive concentration as low as 0.01M, for example.

It has further been observed that such decreased corrosion can be obtained without a significantly decreased rate of reaction. For example, such decreased corrosion rates may be observed with less than 25%, or less than 20%, or less than 15%, or less than 10%, or less than 5% decrease in reaction rate. However, it is contemplated that rather than limited decreases in reaction rates, no decrease in reaction rate or an actual increase in reaction rate may be observed with the embodiments described herein. For example, the decreased corrosion rates may be observed with from a 25% decrease in reaction rate to a 25% increase in reaction rate. In particular, increases in reaction rates can be observed with embodiments utilizing the additive packages over processes utilizing a single additive. Such reaction rates can be observed with all carbonylation catalysts described herein, but are particularly relevant with Ir based catalysts, which tend to exhibit rapid reaction rate reductions upon contact with phosphine oxide. However, embodiments described herein may be capable of use in Ir based catalyst systems with no observable decrease (and potentially an increase as described above) in reaction rate.

The reaction medium may further include an alkyl iodide, such as methyl iodide, for example. The concentration of alkyl iodide in the reaction medium may be from 0.6 wt. % to 36 wt. %, or from 4 wt. % to 24 wt. %, or from 6 wt. % to 20 wt. % based on total weight of reaction medium, for example. Furthermore, the reaction medium may include an alkyl acetate, such as methyl acetate, for example. The concentration of alkyl acetate in the reaction medium may be from 0.6 wt. % to 36 wt. %, or from 2 wt. % to 20 wt. %, or from 2 wt. % to 16 wt. %, or from 3 wt. % to 10 wt. %, or from 2 wt. % to 8 wt. % based on the total weight of the reaction medium, for example. As described previously herein, the introduction of such components to the reaction medium can be via introduction to the reaction medium or in-situ generation, or the like.

It is contemplated that supplemental hydrogen may be supplied to the reaction medium. Supplemental hydrogen may be supplied to the reaction medium to provide a total hydrogen concentration in the reaction medium of from 0.1 mol. % to 5 mol. %, or from 0.3 mol. % to 3 mol. %, for example.

In practice, carbonylation reaction conditions vary depending upon reaction parameters, reactor size and charge and the individual components employed. However, in one or more embodiments, the carbonylation process may be a batch or continuous processes and the carbonylation conditions may include a pressure of from 200 psig (1379 kPa) to 2000 psig (13790 kPa), or from 200 psig (1379 kPa) to 1000 psig (6895 kPa), or from 300 psig (2068 kPa) to 500 psig (3447 kPa), for example and a temperature of from 150° C. to 250° C., or from 170° C. to 220° C., or from 150° C. to 200° C., for example.

Carbonylation processes further include recovering the formed acetic acid from the process. Such recovery can be accomplished by methods which may include, without limitation, separation and/or purification processes (including but not limited to flashing and distillation). Such processes are known to one skilled in the art and therefore are not described in detail herein.

FIG. 1 illustrates a schematic of an embodiment of an acetic acid production process 100. The process 100 is generally described in terms of functional areas, i.e., a reaction area 102, a light-ends area 104, a purification area 106 and a recycle area 108, rather than specific process equipment. Note that the "streams" discussed herein may be part of more than one functional area.

The reaction area 102 may include a reactor 110, a flash vessel 120, equipment associated with the reactor 110 and flash vessel 120, and streams associated with the reactor 110 and flash vessel 120. For example, the reaction area 102 may include reactor 110, flash vessel 120, and streams (or portions of streams) 111, 112, 114, 121, 126, 131, 160, 138, 139, 148. The reactor 110 is a reactor or vessel in which methanol is carbonylated in the presence of a catalyst to form acetic acid at elevated pressure and temperature. The flash vessel 120 is a tank or vessel in which a reaction mixture obtained in the reactor, for example the reactor 110, is at least partially depressurized and/or cooled to form a vapor stream and a liquid stream.

The light-ends area 104 may include a separations column, for example, a light-ends column 130, equipment associated with light-ends column 130, and streams associated with the light-ends column 130. For example, the light-ends area 104 may include light-ends column 130, decanter 134, and streams 126, 131, 132, 133, 135, 136, 138, 139, 160. The light-ends column 130 is a fractioning or distillation column and includes any equipment associated with the column, including but not limited to heat exchangers, decanters, pumps, compressors, valves, and the like.

The purification area 106 may include a drying column 140, optionally, a heavy-ends column 150, equipment associated with drying column 140 and heavy-ends column 150, and streams associated with the drying column 140 and heavy-ends column 150. For example, the purification area 106 may include drying column 140, heavy-ends column 150, and streams 136, 141, 142, 145, 148, 151, 152, 156. The heavy-ends column 150 is a fractioning or distillation column and includes any equipment associated with the column, including but not limited to heat exchangers, decanters, pumps, compressors, valves, and the like.

The recycle area 108 may include process streams recycled to the reaction area 102 and/or light-ends area 104. For example, in FIG. 1, the recycle area 108 may include streams 121, 138, 139, 148.

In an embodiment, the reactor 110 may be configured to receive a carbon monoxide feed stream 114 and a methanol or methanol/methyl acetate feed stream 112. A reaction mixture may be withdrawn from the reactor in stream 111. Other streams may be included, for example, a stream that may recycle a bottoms mixture of the reactor 110 back into the reactor 110, or a stream may be included to release a gas from the reactor 110. Stream 111 may include at least a part of the reaction mixture.

In an embodiment, the flash vessel 120 may be configured to receive stream 111 from the reactor 110. In the flash vessel 120, stream 111 may be separated into a vapor stream 126 and a liquid stream 121. The vapor stream 126 may be communicated to the light-ends column 130, and the liquid stream 121 may be communicated to the reactor 110 (stream 121 may thus be considered in the recycle area 108 and in the reactor area 102). In an embodiment, stream 126 may comprise acetic acid, water, methyl iodide, methyl acetate, HI, and mixtures thereof.

In an embodiment, the light-ends column 130 may include a distillation column and equipment associated with the distillation column including but not limited to a heat exchanger 137, a decanter 134, pumps, compressors, valves, and other related equipment. The light-ends column 130 may be configured to receive stream 126 from the flash vessel 120. Stream 132 includes overhead product from the light-ends column 130, and stream 131 includes bottoms product from the light-ends column 130. Light-ends column 130 may include a decanter 134, and stream 132 may pass into decanter 134.

Stream 135 may emit from decanter 134 and recycle back to the light-ends column 130. Stream 138 may emit from decanter 134 and may recycle back to the reactor 110 via, for example, stream 112 or be combined with any of the other streams that feed the reactor (stream 138 may thus be considered in the recycle area 108, in the light-ends area 104, and in the reactor area 102). Stream 139 may recycle a portion of the light phase of decanter 134 back to the reactor 110 via, for example, stream 112 (stream 139 may thus be considered in the recycle area 108, in the light-ends area 104, and in the reactor area 102). Stream 136 may emit from the light-ends column 130. Other streams may be included, for example, a stream that may recycle a bottoms mixture of the light-ends column 130 back into the light-ends column 130. Any stream received by or emitted from the light-ends column 130 may pass through a pump, compressor, heat exchanger, and the like as is common in the art.

In an embodiment, the drying column 140 may comprise a vessel and equipment associated with the vessel including but not limited to heat exchangers, decanters, pumps, compressors, valves, and the like. The drying column 140 may be configured to receive stream 136 from the light-ends column 130. The drying column 140 may separate components of stream 136 into streams 142 and 141.

Stream 142 may emit from the drying column 140, recycle back to the drying column via stream 145, and/or recycle back to the reactor 110 through stream 148 (via, for example, stream 112). Stream 141 may emit from the drying column 140 and may include de-watered crude acetic acid product. Stream 142 may pass through equipment that is readily available, for example, a heat exchanger or separation vessel before streams 145 or 148 recycle components of stream 142. Other streams may be included, for example, a stream may recycle a bottoms mixture of the drying column 140 back into the drying column 140. Any stream received by or emitted from the drying column 140 may pass through a pump, compressor, heat exchanger, separation vessel, and the like as is common in the art.

The heavy-ends column 150 may include a distillation column and equipment associated with the distillation column including but not limited to heat exchangers, decanters, pumps, compressors, valves, and the like. The heavy-ends column 150 may be configured to receive stream 141 from the drying column 140. The heavy-ends column 150 may separate components from stream 141 into streams 151, 152, and 156. Streams 151 and 152 may be sent to additional processing equipment (not shown) for further processing. Stream 152 may also be recycled, for example, to light-ends column 140. Stream 156 may include acetic acid product.

Suitable alternative embodiments for the acetic acid production system 100 may be found in U.S. Pat. No. 6,552,221, which is herein incorporated by reference.

EXAMPLES

To facilitate a better understanding of the disclosure, the following examples of embodiments are given. In no way should the following examples be read to limit, or to define, the scope of the appended claims.

CORROSION STUDY TEST PROCEDURE: Prepared samples were added to 5 mL heavy walled borosilicate Wheaton vials such that the vials contained a total liquid volume of 4 mL. A glass bead blasted 316L stainless steel coupon of dimensions 0.062" (0.157 cm)×0.30" (0.762 cm)×0.50" (1.27 cm) and of approximately 1 gram in weight was added to each vial. Prior to addition to the vial, the coupons were cleaned by immersion in acetone for 5 minutes, followed by drying and weighing on a 4-figure analytical balance. These vials, charged with liquid and coupon, were then septum sealed and purged with one atmosphere of CO or $N_2$ for 2 minutes followed by placement in a water bath maintained at the specified temperature. After 44-48 hours of heating, the vials were removed from the water bath and allowed to cool. The coupons were removed, soaked in acetone for 5 minutes, dried and re-weighed. The % weight loss of coupons due to corrosion was calculated based on the initial and final weights.

CATALYST STABILITY TEST PROCEDURE: Studies were undertaken to analyze catalyst stability in terms of extent of decay of soluble Rh(I) to Rh(III). The rate and extent of Rh(I) decay in catalyst solutions maintained under flash tank conditions can be monitored by periodic sampling and FTIR analysis. In such a procedure, a stock solution of the active rhodium catalyst was prepared by adding 0.20 g of rhodium (I) dicarbonyl chloride dimer, to 20 mLs of acetic acid and saturating the solution with CO by bubbling one atmosphere of CO through the solution at room temperature for 5 minutes. 0.40 g of lithium iodide was then added and after 10 minutes of stirring, the active Rh catalyst, $[Rh(CO)_2I_2]^-$ formed in quantitative yield. In the present examples, a solution of about 5,000 ppm resulted. For catalyst stability studies, aliquots of this solution were then added to solutions contained in septum sealed vials of the type described in Corrosion Study Test Procedure.

A number of experiments were undertaken to determine the effectiveness of a variety of additives on corrosivity and catalyst stability. Unless specified otherwise, all corrosion studies were performed under the following conditions: 1 atm (101 kPa) CO, 44 hours, 70° C., 0.5M HI, 3.2M $H_2O$, HOAc. Unless specified otherwise, all catalyst stability studies were performed under the following conditions: 1 atm (101 kPa) $N_2$, 70° C., 0.1M HI, 2.0M $H_2O$, HOAc, 2500 ppm Rh.

Batch reactor runs, as described in Examples 7-10, were carried out in a ⅔ filled Hastalloy B2 stirred 300 mL autoclave. The reactor head was equipped with attachments for cooling coils, thermocouples and dip tubes. Loss of vapor to vapor stack was minimized by two in-series condensers.

For batch reactor runs as described in Example 10 where corrosion was being investigated and where no methyl acetate or catalyst were added, the following procedure was followed: the liquid reaction components were charged to the reactor. After leak testing with nitrogen and purging with CO, the reactor and its contents were heated to 175° C. at a CO pressure of 100-200 psig (690-1379 kPa) with agitation. After reaching the specified temperature, the pressure was raised to 400 psig (2758 kPa). After pre-determined run times as described in Example 10, the reactor was cooled to ambient temperature via internal water cooled coil, vented to about 30 psig (207 kPa) through a condenser maintained at −6° C. and then a liquid sample was collected for analysis by ICP.

For batch reactor runs as described in Examples 7-9 where carbonylation rates were being investigated, the following procedure was followed: the liquid reaction components, minus the catalyst, were charged to reactor. After leak testing with nitrogen and purging with CO, the reactor and its contents were heated to 175° C. at a CO pressure of 100-200 psig (690-1379 kPa) with agitation. The reaction was then started by injecting a chosen amount of a solution of rhodium acetate into the reactor, following which the pressure of the reactor was raised to 400 psig (2758 kPa). The reaction was allowed to proceed at constant pressure, which was maintained for 45 minutes by feeding CO from a high pressure reservoir. The pressure drop was converted to the moles of CO reacted using the known reservoir volume. The reactor was cooled and vented as described above prior to sampling for gas chromatographic (GC) analysis.

Due to variations in data software and collection points associated with the batch reactor used to obtain data as described in Examples 8 and 9, total CO consumption was normalized to 2700 seconds by utilizing the data point closest to 2700 seconds, multiplying the value of that data point by 2700 and then dividing by the actual time of the utilized data point. Further, as the volume of solution in those experiments described in Examples 8 & 9 was about 210 mLs, total consumption of feedstock (0.6M methyl acetate) is associated with consumption of about 126 mmoles of CO. This represents a 100% yield and initial carbonylation rates associated with CO uptake in the first several minutes of a batch reactor run can be expressed in various units such as mol/l/hr (often referred to as STY or space time yield) or mmol/s or mM/s. These units are mutually interchangeable for either CO consumed or acetic acid formed.

Example 1

Numerous samples were prepared and studied for corrosion. Table 1 contains the coupon % weight loss data for experiments in which hydrogen iodide was present as indicated in the table. The data show that the additives disclosed herein are effective as corrosion inhibitor. However, it is to be noted that the reproducibility of the test method was tested over a several month period. The data shows coupon % weight loss data for control experiments in which no additive/potential corrosion inhibitor was present and for additional repeat experiments with various additives. Data from these experiments, which were widely spaced in time, show an unambiguous and consistent trend in which extent of corrosion is always greatest when no additive is present. For comparative purposes and to ensure maximum accuracy, a control vial containing no additive was generally included in every run. Therefore, data sometimes includes slightly differing values for the control experiment.

The data in Table 1 show that addition of just 0.01 molar equivalent of BAPO to a Cyanex® 923 solution leads to a remarkable 10-fold decrease in corrosion rate.

It was further observed that (as demonstrated by the BAPO without secondary additive results) the experienced corrosion improvement was not solely associated with water concentrations but rather the choice of additive and concentration among other variables.

It was further observed that the corrosion inhibition effect demonstrated under both a CO and $N_2$ atmosphere shows that such corrosion inhibition is not limited to the reactor but is also in effect in vessels such as flash tanks and purification columns where no CO is present.

To demonstrate that the above reported corrosion inhibition effect is unexpected and unique, similar corrosion experiments were carried out with similarly weakly basic sulfones and sulfoxides as shown in Table 2. As the data show, either independently or in combination with Cyanex® 923, corrosion rates associated with these sulfones and sulfoxides are at least an order of magnitude higher than for BAPO.

TABLE 1

| Primary Additive (A1) | Molarity A1 (M) | Secondary Additive (A2) | Molarity A2 (M) | HI Conc (M) | $H_2O$ Conc (wt. %) | Corrosion (% loss) |
|---|---|---|---|---|---|---|
| None[1] | N/A | None | N/A | 0.5 | 3.2 | 0.516 |
| None[1] | N/A | None | N/A | 0.5 | 3.2 | 0.525 |
| Cyanex ® 923[1] | 1.0 | None | N/A | 0.5 | 3.2 | 0.181 |
| Cyanex ® 923[1] | 0.99 | BAPO | 0.01 | 0.5 | 3.2 | 0.018 |
| Cyanex ® 923[1] | 0.98 | BAPO | 0.02 | 0.5 | 3.2 | 0.018 |
| Cyanex ® 923[1] | 0.95 | BAPO | 0.05 | 0.5 | 3.2 | 0 |
| Cyanex ® 923[1] | 0.8 | BAPO | 0.2 | 0.5 | 3.2 | 0 |
| Cyanex ® 923[1] | 0.6 | BAPO | 0.4 | 0.5 | 3.2 | 0.009 |
| BAPO[1] | 0.8 | Cyanex ® 923 | 0.2 | 0.5 | 3.2 | 0.009 |
| None[1] | N/A | None | N/A | 0.5 | 3.2 | 0.38 |
| TBPO[1] | 0.98 | None | N/A | 0.5 | 3.2 | 0.342 |
| TBPO[1] | 0.84 | BAPO | 0.1 | 0.5 | 3.2 | 0 |
| TBPO[1] | 0.68 | BAPO | 0.29 | 0.5 | 3.2 | 0 |
| TBPO[1] | 0.49 | BAPO | 0.48 | 0.5 | 3.2 | 0.009 |
| BAPO[1] | 0.68 | TBPO | 0.27 | 0.5 | 3.2 | 0 |
| None[1] | N/A | None | N/A | 0.5 | 3.2 | 0.380 |
| BAPO[1] | 0.005 | TMDPO | 0.005 | 0.5 | 3.2 | 0.296 |
| BAPO[1] | 0.01 | TMDPO | 0.01 | 0.5 | 3.2 | 0.054 |
| TBPO[1] | 1.0 | None | N/A | 0.5 | 3.2 | 0.276 |
| TBPO[1] | 0.9 | TMDPO | 0.1 | 0.5 | 3.2 | 0.253 |
| TBPO[1] | 0.7 | TMDPO | 0.3 | 0.5 | 3.2 | 0.241 |
| TMDPO[1] | 0.7 | TBPO | 0.3 | 0.5 | 3.2 | 0.118 |
| TMDPO[1] | 1.0 | None | N/A | 0.5 | 3.2 | 0.018 |
| None[1] | N/A | None | N/A | 0.5 | 3.2 | 0.516 |
| Cyanex ® 923[1] | 0.8 | None | N/A | 0.5 | 3.2 | 0.248 |
| Cyanex ® 923[1] | 0.8 | TMDPO | 0.2 | 0.5 | 3.2 | 0.226 |
| Cyanex ® 923[1] | 0.2 | None | N/A | 0.5 | 3.2 | 0.490 |
| TMDPO[1] | 0.8 | Cyanex ® 923 | 0.2 | 0.5 | 3.2 | 0.045 |
| None[1] | N/A | None | N/A | 0.5 | 3.2 | 0.480 |
| TPPO[1] | 1.0 | None | N/A | 0.5 | 3.2 | 0.107 |
| TPPO[1] | 0.99 | BAPO | 0.01 | 0.5 | 3.2 | 0.018 |
| TPPO[1] | 0.95 | BAPO | 0.05 | 0.5 | 3.2 | 0.019 |
| TPPO[1] | 0.90 | BAPO | 0.10 | 0.5 | 3.2 | 0.000 |
| Cyanex ® 923[1] | 1.0 | None | N/A | 0.5 | 3.2 | 0.242 |
| Cyanex ® 923[1] | 0.75 | TPPO | 0.25 | 0.5 | 3.2 | 0.188 |
| Cyanex ® 923[1] | 0.50 | TPPO | 0.50 | 0.5 | 3.2 | 0.135 |
| TPPO[1] | 0.75 | Cyanex ® 923[1] | 0.25 | 0.5 | 3.2 | 0.090 |
| BAPO[1] | 0.025 | None | N/A | 0.5 | 3.2 | 0.018 |
| BAPO[1] | 0.025 | None | N/A | 0.5 | 5.0 | 0.000 |
| BAPO[1] | 0.025 | None | N/A | 0.5 | 7.0 | 0.000 |
| BAPO[1] | 0.025 | None | N/A | 0.5 | 10.0 | 0.009 |
| TPPO[2] | 1.0 | BAPO | 0.01 | 0.5 | 3.2 | 0.018 |
| TBPO[2] | 1.0 | BAPO | 0.01 | 0.5 | 3.2 | 0.009 |
| Cyanex ® 923[2] | 1.0 | BAPO | 0.01 | 0.5 | 3.2 | 0.009 |
| Cyanex ® 923[2] | 1.0 | TMDPO | 0.01 | 0.5 | 3.2 | 0.144 |

[1] 1 atm (101 kPa) CO, 70° C., 48 hours, HOAc; 2.1 atm (101 kPa) $N_2$, 75° C., 48 hours, HOAc
[2] 1 atm (101 kPa) $N_2$, 75° C., 48 hours, HOAc

TABLE 2

| Primary Additive (A1) | Molarity A1 (M) | Secondary Additive (A2) | Molarity A2 (M) | HI Conc (M) | H$_2$O Conc (wt. %) | Corrosion (% loss) |
|---|---|---|---|---|---|---|
| None[1] | N/A | None | N/A | 0.5 | 3.2 | 0.48 |
| None[1] | N/A | DPSO | 1.0 | 0.5 | 3.2 | 0.559 |
| None[1] | N/A | PSOX | 1.0 | 0.5 | 3.2 | 2.59 |
| None[1] | N/A | MePSO | 1.0 | 0.5 | 3.2 | 0.46 |
| Cyanex® 923[1] | 0.95 | DPSO | 0.05 | 0.5 | 3.2 | 0.28 |
| Cyanex® 923[1] | 0.95 | PSOX | 0.05 | 0.5 | 3.2 | 1.01 |
| Cyanex® 923[1] | 0.95 | MePSO | 0.05 | 0.5 | 3.2 | 0.235 |

[1] 1 atm (101 kPa) CO, 70° C., 48 hours, HOAc;
[2] DPSO = diphenyl sulfone, MePSO = methylphenyl sulfone, PSOX = diphenyl sulfoxide Table 3 demonstrates the results from an additive package including 3 additives.

TABLE 3

| Primary Additive (A1) | Molarity A1 (M) | Secondary Additive (A2) | Molarity A2 (M) | Secondary Additive (A3) | Molarity A3 (M) | HI Conc (M) | H$_2$O Conc (wt. %) | Corrosion (% loss) |
|---|---|---|---|---|---|---|---|---|
| None[1] | N/A | None | N/A | None | N/A | 0.5 | 3.2 | 0.380 |
| Cyanex® 923[1] | 1.0 | None | N/A | None | N/A | 0.5 | 3.2 | 0.181 |
| Cyanex® 923[1] | 1.0 | BAPO | 0.01 | TMDPO | 0.01 | 0.5 | 3.2 | 0.009 |
| Cyanex® 923[1] | 1.0 | BAPO | 0.005 | TMDPO | 0.005 | 0.5 | 3.2 | 0.027 |

[1] 1 atm (101 kPa) CO, 70° C., 48 hours, HOAc

Example 2

Numerous samples were prepared and studied for corrosion. Table 4 contains the coupon % weight loss data for control experiments in which no additive/potential corrosion inhibitor was present while Table 5 contains the coupon % weight loss for repeat experiments in which hydrogen iodide was present. Data from these experiments show that even an iodide free system can exhibit a measurable level of corrosion. However, the data further show that the stabilizer disclosed herein is an effective corrosion inhibitor in both environments.

TABLE 4

| Stabilizer | Molarity | Corrosion (%) |
|---|---|---|
| None | N/A | 0.127 |
| None | N/A | 0.136 |
| Cyanex® 923 | 0.5 | 0.027 |

0.0M HI, 3.2 wt. % H$_2$O, HOAc, CO, 70° C., 48 hours

TABLE 5

| Stabilizer | Molarity | Corrosion (%) |
|---|---|---|
| None | N/A | 0.516 |
| None | N/A | 0.525 |
| Cyanex® 923 | 0.25 | 0.490 |
| Cyanex® 923 | 0.5 | 0.327 |
| Cyanex® 923 | 1 | 0.181 |

0.5M HI, 3.2 wt. % H$_2$O, HOAc, CO, 70° C., 48 hours

Example 3

High concentrations (5 wt. %) and low concentration (1850 ppm) HI aqueous solutions were prepared and extracted with various ratios of Cyanex® 923. After shaking, all solutions separated into an organic, low density (0.88 g/mL) Cyanex® 923 light phase and an aqueous heavy phase. Aliquots of aqueous heavy phase were removed and analyzed by UV/Vis for HI content and by FTIR to determine concentration (if any) of Cyanex® 923 in aqueous phase. The data in Table 6 below show that for an 1850 ppm HI solution, 85% of HI is extracted from the aqueous phase (via complexation) into the organic Cyanex® 923 light phase at a Cyanex® 923/H$_2$O ratio of only 0.26.

TABLE 6

| Volumetric ratio Cyanex® 923 | PPM HI | Cyanex® 923 in light phase (wt. %) |
|---|---|---|
| 0 | 1850 | 0 |
| 0.48 | 939 | 0.02 |
| 0.1 | 701 | 0.1 |
| 0.15 | 492 | 0.32 |
| 0.21 | 356 | 0.53 |
| 0.26 | 308 | 0.62 |

The same procedure was repeated with 5 wt % HI, resulting in a greater than 90% extraction of the HI at 0.88 ratio, see, Table 7.

TABLE 7

| Volumetric ratio Cyanex® 923 | Wt % HI | Cyanex® 923 in light phase (wt. %) |
|---|---|---|
| 0 | 4.97 | 0 |
| 0.17 | 3.75 | 1 |
| 0.35 | 2.2 | 2.1 |
| 0.53 | 1.13 | 3.1 |
| 0.7 | 0.76 | 4.2 |
| 0.88 | 0.41 | 5.2 |

Example 4

Numerous samples were prepared and studied for corrosion. Table 8 contains the coupon % weight loss data for experiments. The data show that the stabilizer disclosed herein is an effective corrosion inhibitor.

TABLE 8

| Stabilizer | Molarity (M) | Corrosion |
|---|---|---|
| None | N/A | 0.380 |
| TMDPO | 0.053 | 0.036 |
| TMDPO | 0.096 | 0.027 |
| TMDPO | 0.149 | 0.027 |
| TMDPO | 0.23 | 0.018 |
| TMDPO | 0.46 | 0.044 |
| TMDPO | 0.75 | 0.018 |
| TMDPO | 1.01 | 0.018 |
| BAPO | 0.010 | 0.018 |
| BAPO | 0.046 | 0.027 |
| BAPO | 0.098 | 0.027 |
| BAPO | 0.149 | 0.000 |
| BAPO | 0.190 | 0.009 |
| BAPO | 0.460 | 0.036 |
| BAPO | 0.710 | 0.063 |
| BAPO | 0.940 | 0.072 |

0.5M HI, 3.2 wt. % $H_2O$, 1 atm (101 kPa) CO, 70° C., 48 hours, HOAc

Example 5

Figure 2:
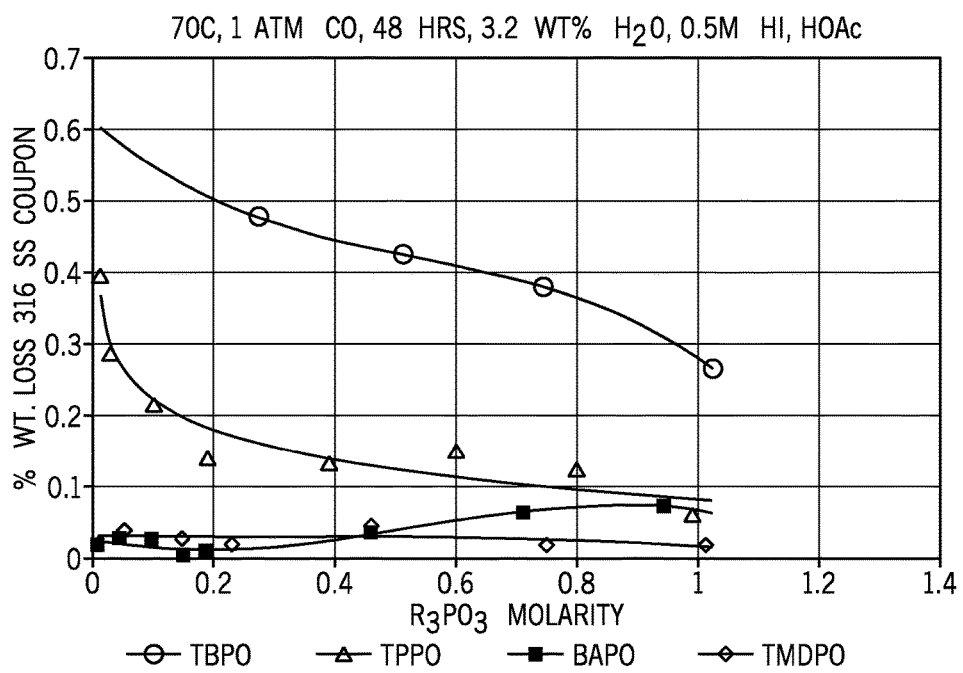
FIG. 2 illustrates corrosion data associated with examples utilizing embodiments of the disclosed process.

FIG. 2 shows corrosion data obtained with 316 stainless steel coupons (via the process described for Example 4). The data show the corrosion inhibition ability of TMDPO and BAPO and that the extent of corrosion inhibition does not appear to be dependent on any particular stoichiometry between the additive and HI. This latter finding is advantageous as it suggests that only low concentrations of additive (as compared to alternative additives TBPO and TPPO) in the process will be required to obtain maximum corrosion inhibition.

Example 6

Numerous samples were prepared and studied for corrosion. Table 9 contains the coupon % weight loss data for experiments in which hydrogen iodide was present as indicated in the table. The data show that the additive disclosed herein is an effective corrosion inhibitor.

TABLE 9

| Additive | HI Conc (M) | H2O Conc (wt. %) | Molarity (M) | Corrosion (% loss) |
|---|---|---|---|---|
| None[1] | 0.5 | 3.2 | N/A | 0.460 |
| TPPO[1] | 0.5 | 3.2 | 0.009 | 0.397 |
| TPPO[1] | 0.5 | 3.2 | 0.025 | 0.288 |
| TPPO[1] | 0.5 | 3.2 | 0.050 | 0.296 |
| TPPO[1] | 0.5 | 3.2 | 0.100 | 0.216 |
| TPPO[1] | 0.5 | 3.2 | 0.240 | 0.177 |
| TPPO[1] | 0.5 | 3.2 | 0.490 | 0.108 |
| None[1] | 0 | 3.2 | N/A | 0.127 |
| TPPO[1] | 0 | 3.2 | 0.5 | 0.009 |
| TBPO[1] | 0.5 | 3.2 | 0.025 | 0.429 |
| TBPO[1] | 0.5 | 3.2 | 0.1 | 0.425 |
| TBPO[1] | 0.5 | 3.2 | 0.25 | 0.477 |
| TBPO[1] | 0.5 | 3.2 | 0.51 | 0.425 |
| TBPO[1] | 0.5 | 3.2 | 0.74 | 0.381 |
| TBPO[1] | 0.5 | 3.2 | 0.95 | 0.244 |
| TBPO[1] | 0.5 | 3.2 | 1.02 | 0.266 |
| TPPO[2] | 0.5 | 3.2 | 0.25 | 0.246 |
| TPPO[2] | 0.5 | 3.2 | 0.5 | 0.202 |
| TPPO[2] | 0.5 | 3.2 | 1.0 | 0.15 |

[1] 1 atm (101 kPa) CO, 70° C., 48 hours, HOAc;
[2] 1 atm (101 kPa) $N_2$, 75° C., 48 hours, HOAc It was unexpectedly observed that when variable additive concentration was used at a fixed water concentration, a TPPO concentration as low as 0.01M could provide significant corrosion inhibition. It was further observed that the corrosion inhibition effect demonstrated under both a CO and $N_2$ atmosphere shows that such corrosion inhibition is not limited to the reactor but is also in effect in vessels such as flash tanks and purification columns where no CO is present.

Example 7

Figure 3:
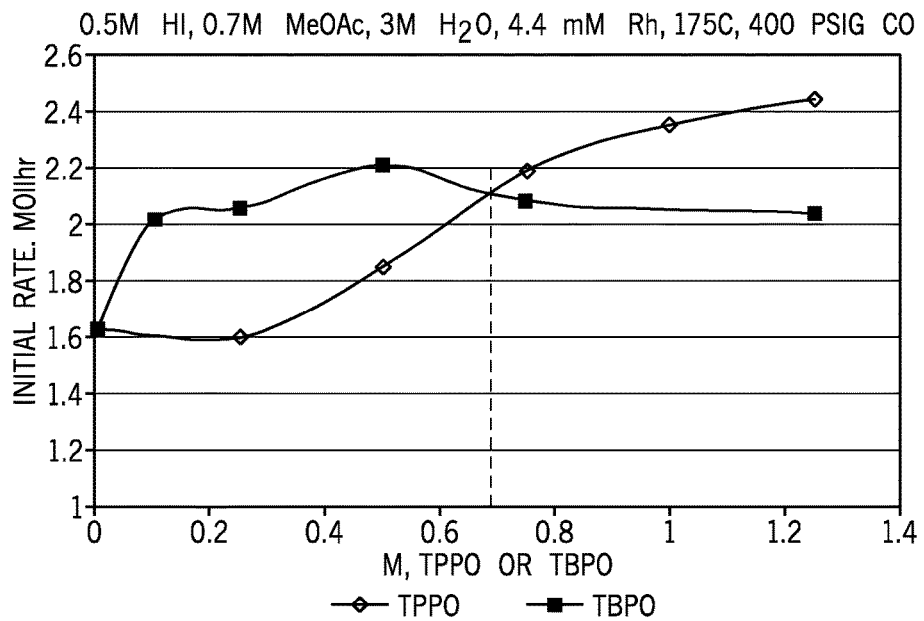
FIG. 3 illustrates rate data associated with examples utilizing embodiments of the disclosed process.

Batch reactor runs were carried out in which TPPO or TBPO was varied from 0 to 1.25M (conditions for these runs are shown in FIG. 3). Three critical measurements were carried out per run. The first of these was "initial rate" which is a measure of space time yield (STY) in the first couple of minutes of run time where initial component concentrations have not deviated significantly from starting values. The second of these was "% yield" which is a measurement of acetic actually produced versus the theoretical maximum. A yield of less than 100% is an indication that loss of catalyst activity prevented complete consumption of the feed that was loaded in the reactor. All runs were carried out with starting concentrations of 0.5M HI and 0.7M methyl acetate. At process temperature, these two components equilibrate rapidly to 0.5M MeI, 0.5M HOAc and the remaining 0.2M MeOAc. The subsequent initial rate is then a function of MeI concentration and active catalyst concentration. As stabilizers are capable of competing with MeOAc for interaction with HI, a third critical measurement was "initial MeI concentration" just prior to catalyst injection.

Figure 4:
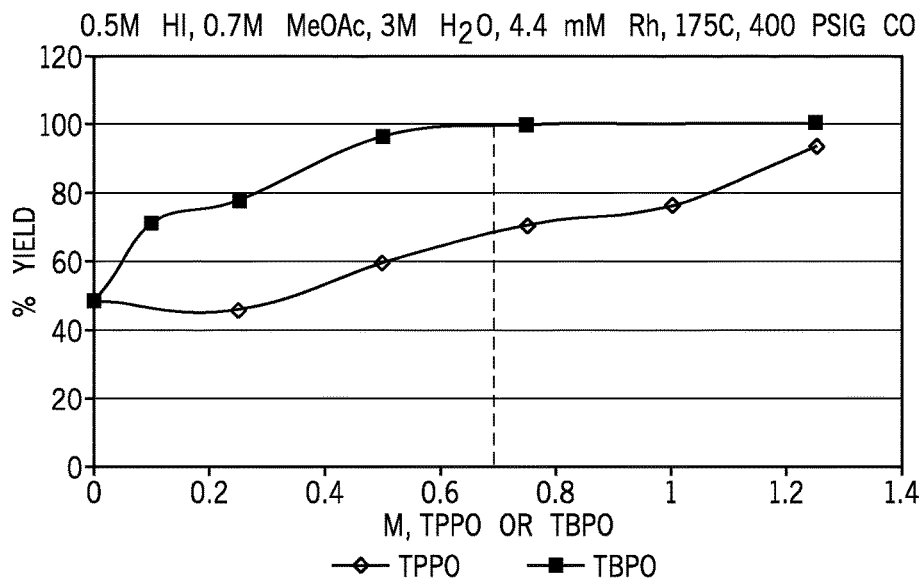
FIG. 4 illustrates % yield data associated with examples utilizing embodiments of the disclosed process.

Data in FIG. 3 for initial rate measurements in which each data point is associated with a separate batch reactor experiment show some surprising trends. While initial rate increases directionally for all concentrations of TPPO, such is not the case for TBPO, where instead a maximum STY is reached, followed by a rate decrease. The transition point of equivalent rate at about 0.7M phosphine oxide is indicated by a vertical dashed line. The % yields associated with the same runs are shown in FIG. 4.

The cumulative data show that there exists a window of phosphine oxide concentration where TBPO can allow both enhanced catalyst stability as measured by % yield and enhanced rate.

Example 8

A series of batch reactor runs were carried out to compare the ability of individual additives or additive combinations to stabilize the active catalyst relative to TPPO. Conditions associated with these runs are shown at the bottom of Table 10. Data in Table 10 are associated with various concentrations of Cyanex 923 and TPPO, present individually or as combinations. It was observed that certain mixtures of Cyanex 923 and TPPO provide equivalent or improved catalyst performance in terms of normalized CO consumption at lower total phosphine oxide concentrations than with TPPO alone. For example, an additive mixture of 0.1M Cyanex 923 and 0.1M TPPO is associated with a higher CO consumption than with 0.4M TPPO. In addition, an equivalent initial rate is associated with the same comparison.

Figure 5:
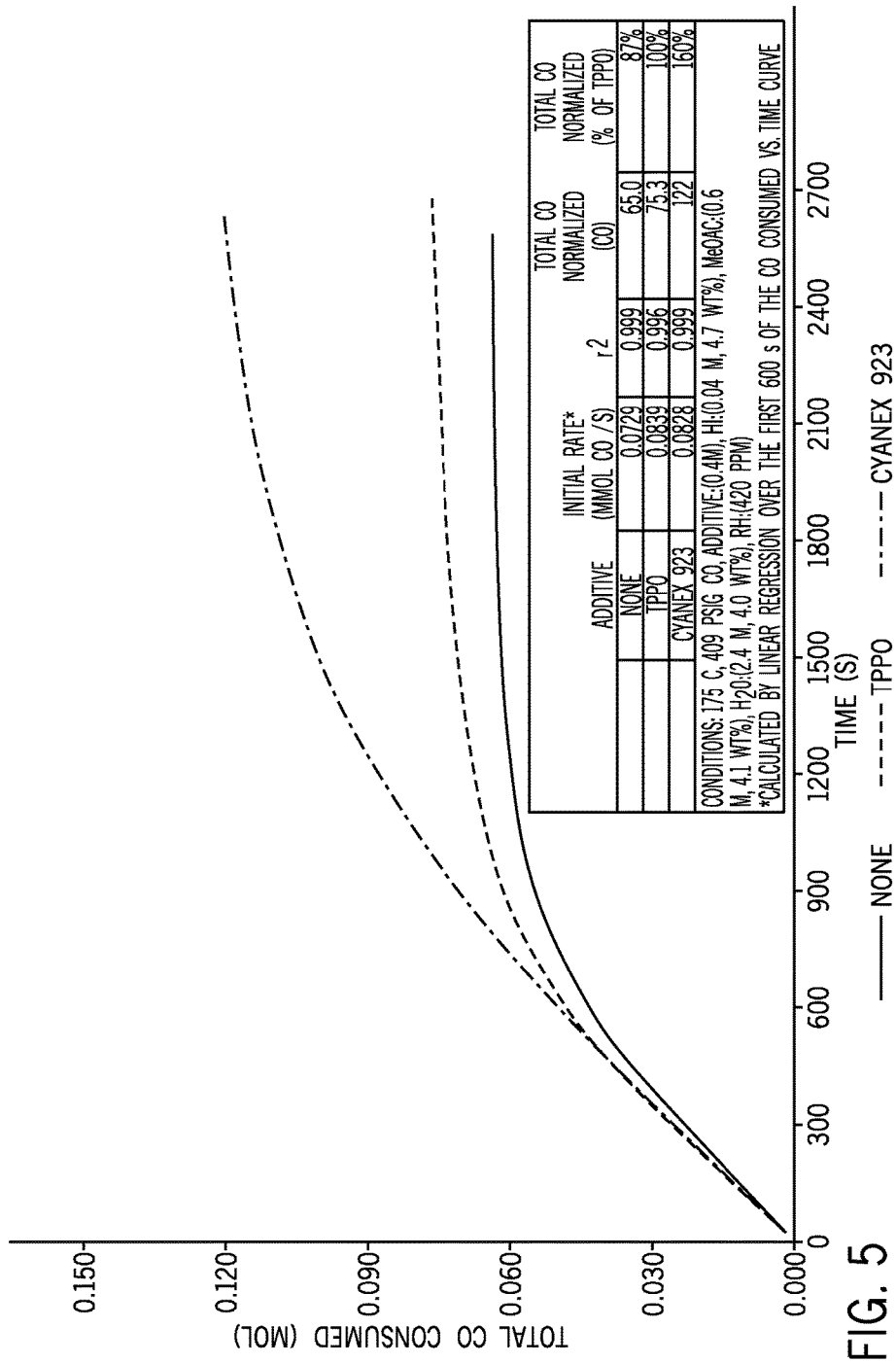
FIG. 5 illustrates data associated with examples utilizing embodiments of the disclosed process.

Referring to FIG. 5 which contains data for 3 comparative batch reactor runs carried out with no additive, 0.4M TPPO or 0.4M Cyanex 923, it can be seen that TPPO allows a 15% increase in initial rate and 16% increase in total CO consumption relative to no additive. Cyanex 923 exhibits a similar initial rate to TPPO and a 60% increase in total CO consumption.

Figure 6:
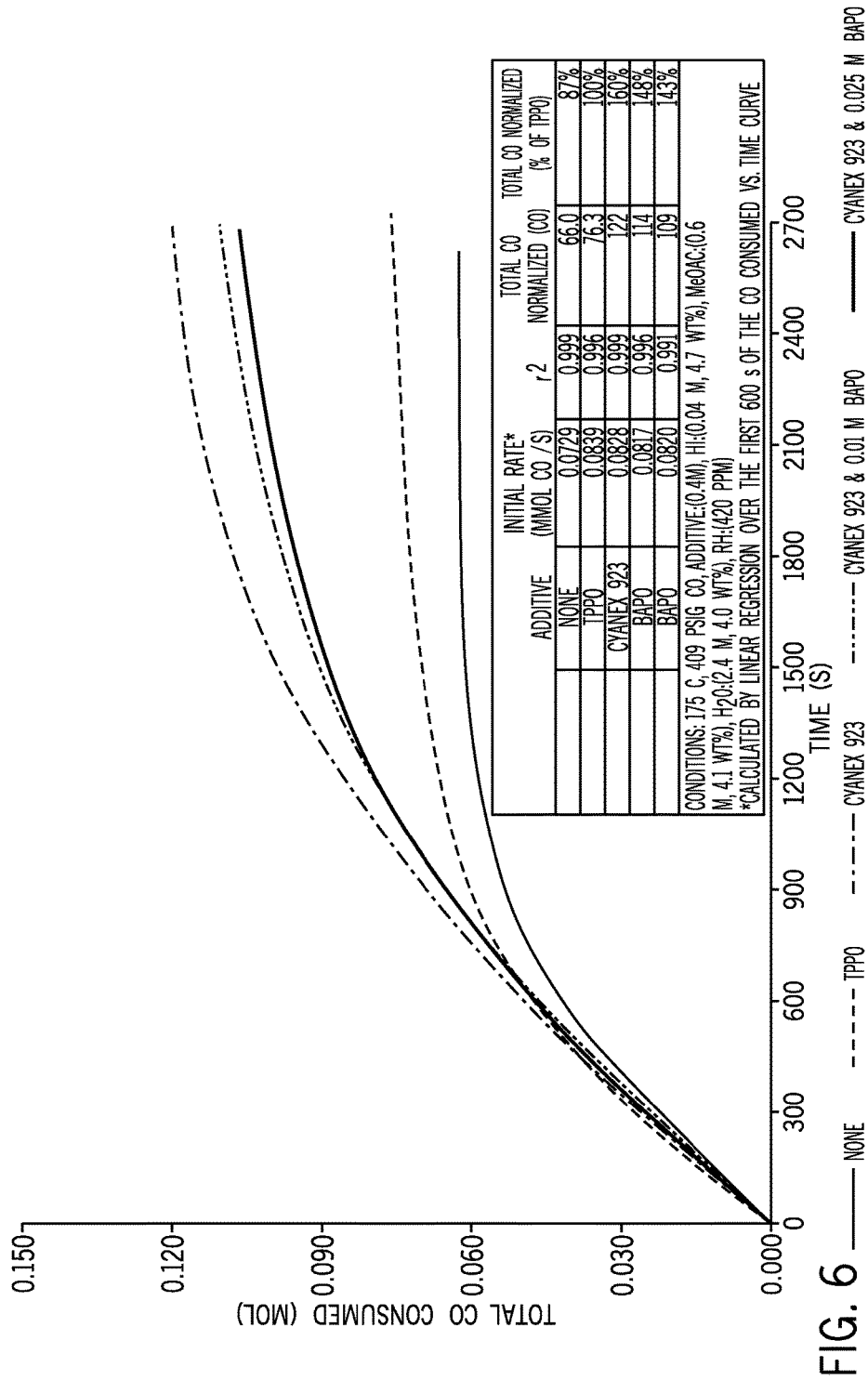
FIG. 6 illustrates data associated with examples utilizing embodiments of the disclosed process.

Referring to FIG. 6, it can be seen that additive mixtures of Cyanex 923 and BAPO have equivalent initial rates and close to equivalent total CO consumption relative to Cyanex 923 as the sole additive.

Figure 7:
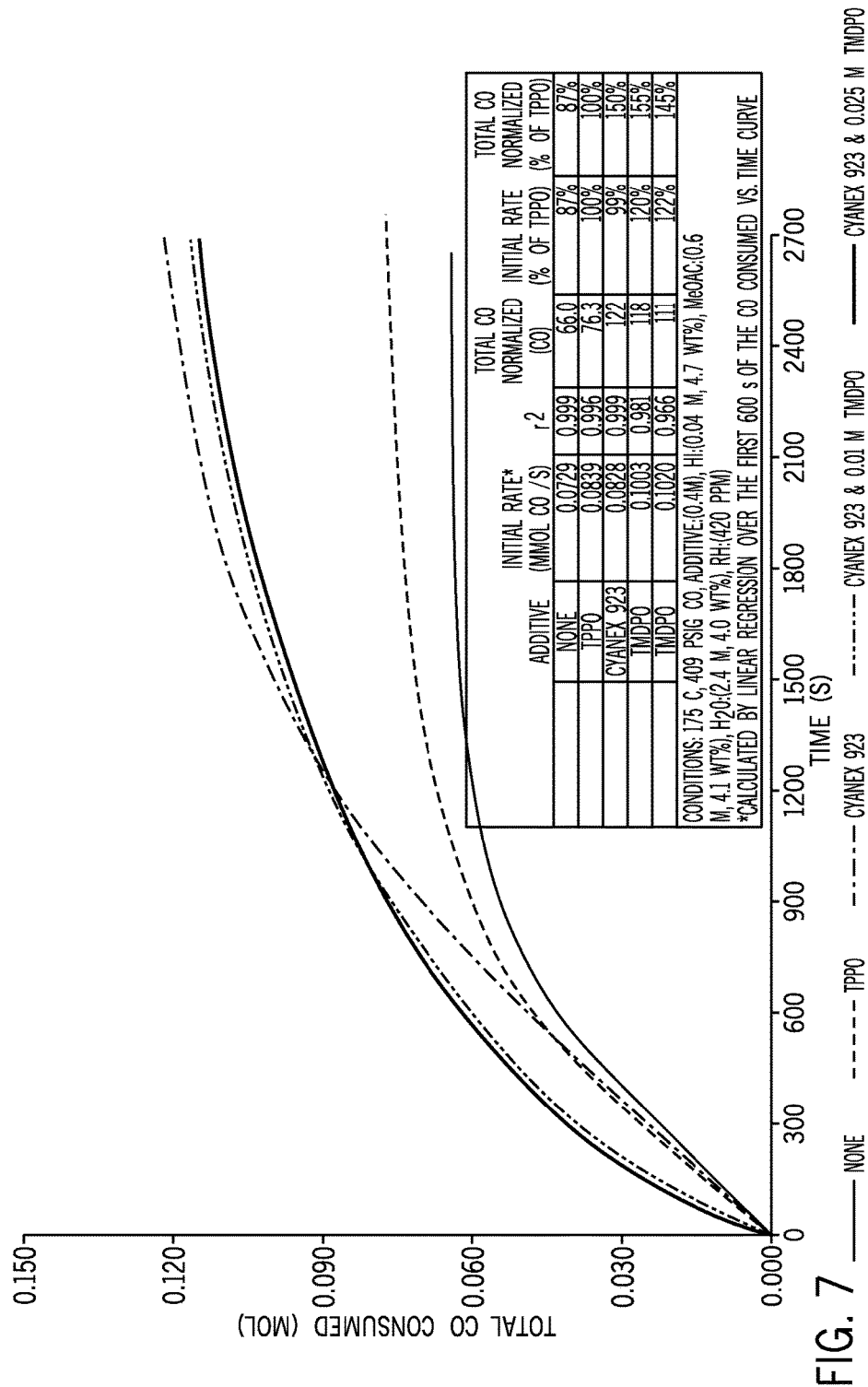
FIG. 7 illustrates data associated with examples utilizing embodiments of the disclosed process.

Referring to FIG. 7, it can be seen that mixtures of Cyanex 923 and TMDPO allow total CO consumption equivalent to Cyanex 923 as the sole additive. FIG. 7 also shows that, unexpectedly, the presence of TMDPO in combination with Cyanex 923 allows an increase of about 20% in the initial rate of reaction. When combined with the greatly decreased corrosion rates for similar mixtures shown in Tables 1 and 3, these data show that such mixtures have multiple beneficial effects relative to individual additives.

TABLE 10

| Cyanex ®923 (M) | TPPO (M) | Initial Rate (mmol/s) | Initial Rate (mM/s) | Total CO Norm (mmol) |
|---|---|---|---|---|
| 0 | 0 | 0.0729 | 0.347 | 66.0 |
| 0 | 0.2 | 0.0764 | 0.364 | 72.6 |
| 0 | 0.4 | 0.0839 | 0.400 | 76.3 |
| 0 | 0.6 | 0.0841 | 0.400 | 88.6 |
| 0 | 0.8 | 0.0902 | 0.430 | 96.0 |
| 0.1 | 0.1 | 0.0842 | 0.401 | 84.8 |
| 0.1 | 0.4 | 0.0868 | 0.413 | 94.1 |
| 0.2 | 0 | 0.081 | 0.386 | 101.0 |
| 0.25 | 0.25 | 0.0899 | 0.428 | 114.0 |
| 0.4 | 0 | 0.0828 | 0.394 | 122.0 |
| 0.4 | 0.1 | 0.0796 | 0.379 | 114.0 |
| 0.4 | 0.4 | 0.0773 | 0.368 | 126.0 |
| 0.6 | 0 | 0.0768 | 0.366 | 136.0 |
| 0.8 | 0 | 0.0794 | 0.378 | 124.0 |
| 0.9 | 0 | 0.0781 | 0.372 | 126.0 |

400 psig (2758 kPa) CO, 0.4M HI, 0.6M MeOAc, 2.4M $H_2O$, 420 ppm Rh

Example 9

A number of batch reactor runs were carried out under conditions similar to those reported in FIG. 5. Unlike all other batch reactor runs described above which had a set duration of about 45 minutes, these runs were of variable duration, ranging from 3 minutes to 30 minutes. At run termination, the reactor was quickly cooled, vented and sampled for gas chromatographic and infrared analysis. Infrared analysis allows quantification of the Rh species, commonly referred to as Rh (I) that is active for carbonylation. GC analysis allows quantification of methyl acetate and methyl iodide, the two "methyl" containing components that are carbonylated to acetic acid.

The catalyst data in Table 11 show that for runs with no additive or TPPO, less than 50% of Rh is active after only 5 minutes of run time. In contrast over 85% of Rh is active after 5 minutes of run time with Cyanex®923 present. This trend is maintained for comparative runs with several different run times. These infrared data confirm the enhanced catalyst stabilization conferred by Cyanex®923 and inferred from the data described in Example 8.

Figure 8:
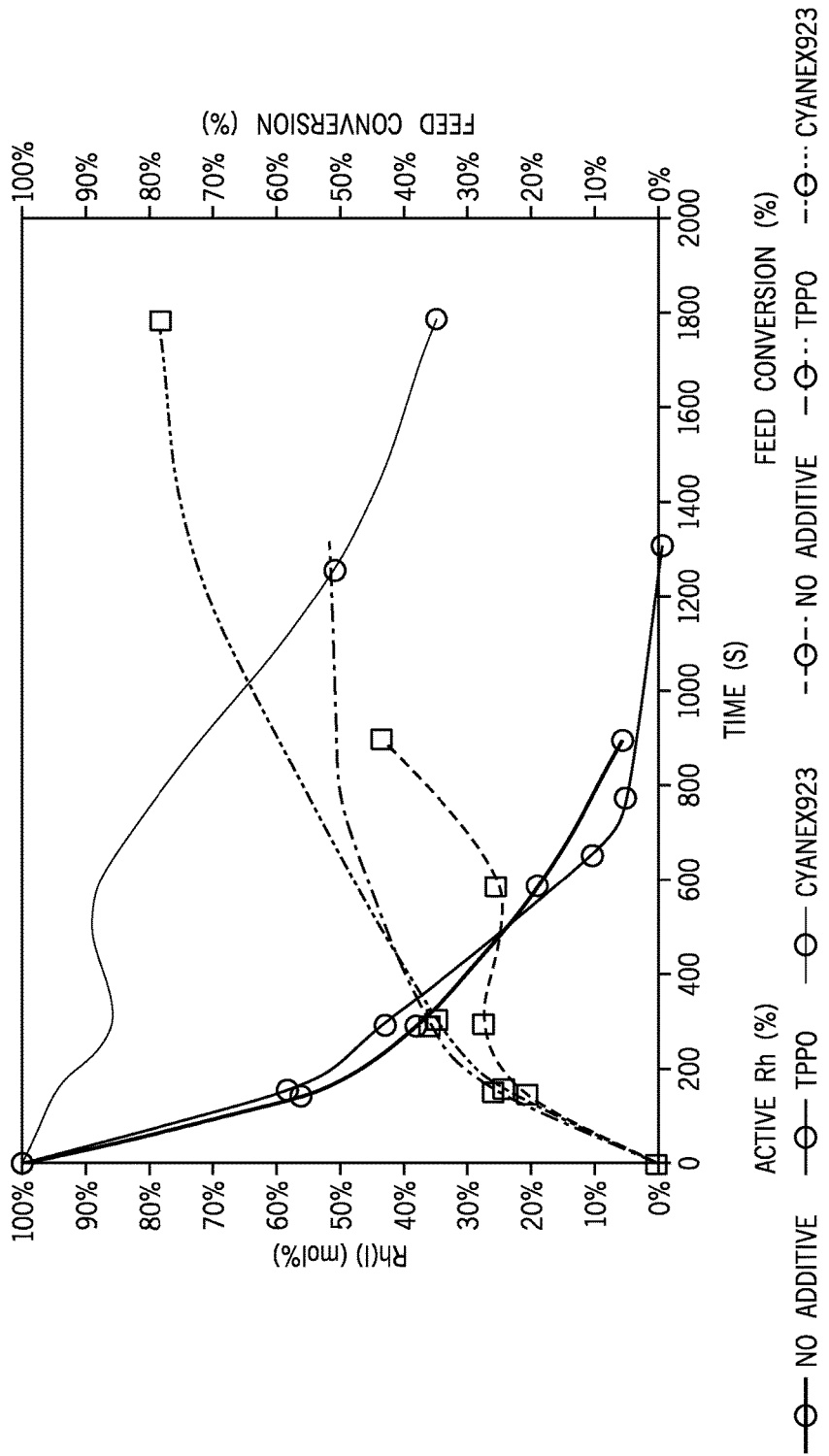
FIG. 8 illustrates % feed conversion associated with examples utilizing embodiments of the disclosed process.

The methyl iodide and methyl acetate data in Table 11 allow an alternative method to CO consumption for calculation of extent of feed conversion. As initial "methyl" was 0.6M, any subsequent decrease in this value is associated with carbonylation to acetic acid. Percent (%) active rhodium and % feed conversion are plotted as a function of run time in FIG. 8. The trend lines indicate that when active rhodium drops below about 40-50%, the rate of acetic acid production begins to taper off and the initially similar feed conversion curves begin to diverge.

TABLE 11

| Additive | Time (s) | Rh(I) (%) | MeI (M) | MeOAc (M) | Feed Conversion (%) |
|---|---|---|---|---|---|
| None | 0 | 100 | 0.001 | 0 | 0 |
| None | 150 | 56 | 0.137 | 0.137 | 20 |
| None | 305 | 38 | 0.103 | 0.103 | 27 |
| None | 600 | 19 | 0.119 | 0.119 | 25 |
| None | 912 | 6 | 0.008 | 0.008 | 44 |
| TPPO | 0 | 100 | 0.219 | 0.219 | 0 |
| TPPO | 161 | 58 | 0.119 | 0.119 | 26 |
| TPPO | 301 | 43 | 0.072 | 0.072 | 36 |
| TPPO | 668 | 10 | 0.016 | 0.016 | 48 |
| TPPO | 783 | 5 | 0.011 | 0.011 | 50 |
| TPPO | 1341 | 0 | 0.010 | 0.010 | 53 |
| Cyanex ®923 | 0 | 100 | 0.220 | 0.220 | 0 |
| Cyanex ®923 | 162 | 95 | 0.190 | 0.190 | 24 |
| Cyanex ®923 | 311 | 86 | 0.140 | 0.140 | 35 |
| Cyanex ®923 | 618 | 88 | 0.078 | 0.078 | 49 |
| Cyanex ®923 | 1279 | 51 | 0.010 | 0.010 | 73 |
| Cyanex ®923 | 1814 | 36 | 0.008 | 0.008 | 80 |

Example 10

Figure 9:
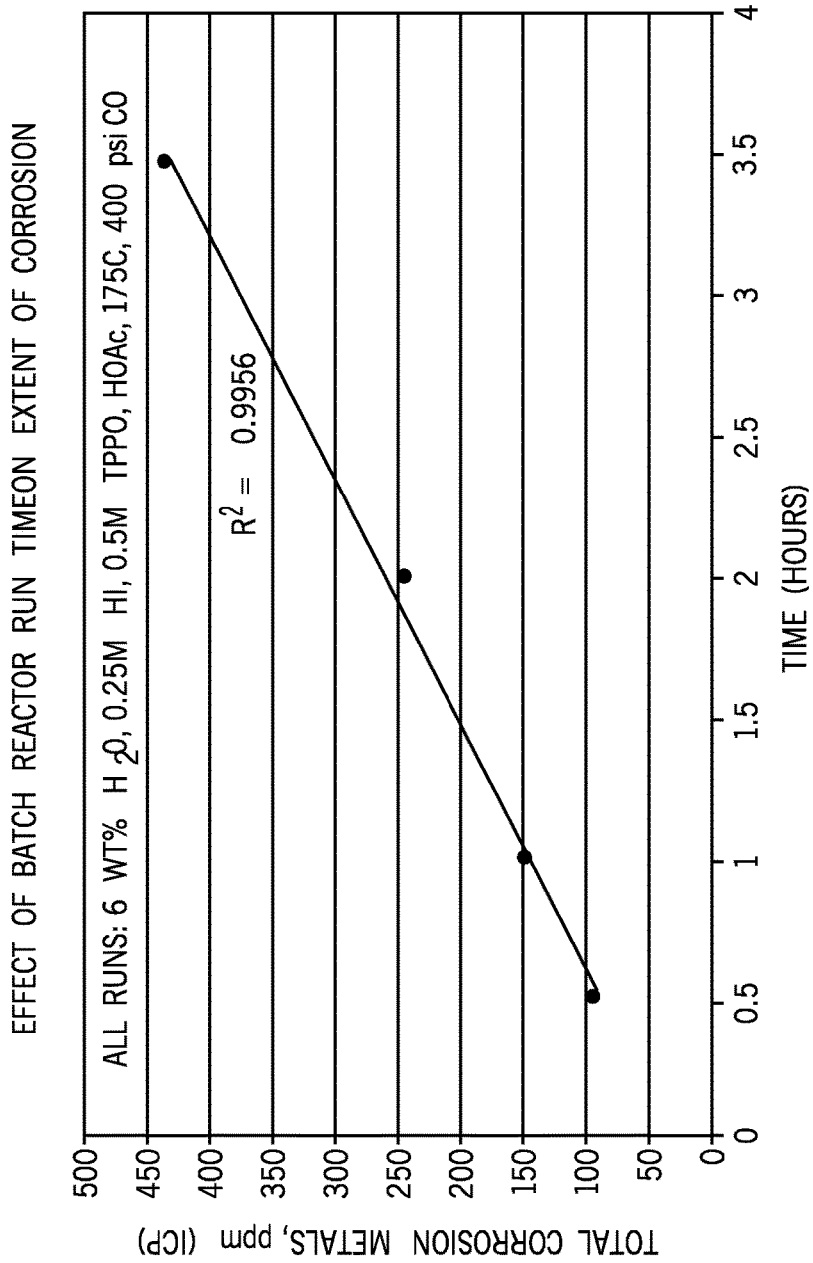
FIG. 9 illustrates data associated with examples utilizing embodiments of the disclosed process.

A new batch reactor based method was investigated as a possible method of determining corrosion rates. These runs were dedicated to measuring a single variable, corrosion. In this method, no catalyst or methyl feed stock are present. These two components are not anticipated to have any effect on corrosion and therefore their absence did not impact results. Without catalyst or feedstock, steady state conditions are observed in the reactor and corrosion rates of the internal surface of the reactor were directly correlated to the starting solution chemical composition. It was unexpectedly found that the large internal surface area of the reactor (up to 3 orders of magnitude greater than corrosion coupons) leads to sufficient corrosion as to be measured by ICP of reactor solutions in as little as 1 hour of heating and pressurization. Repeat runs were carried out ranging in duration from 0.5 to 3.5 hours with aliquots at run termination being analyzed by ICP for corrosion metal concentration (ppm). The data in Table 12 and in FIG. 9 indicate that the extent of corrosion is linear in the 0.5-3.5 hour range.

TABLE 12

| HI (M) | TPPO (M) | Run Time (hrs) | Fe | Cr | Ni | Mo | Total |
|---|---|---|---|---|---|---|---|
| 0.25 | 0.25 | 3.5 | 42 | 72 | 285 | 61 | 440 |
| 0.25 | 0.25 | 2 | 26 | 40 | 144 | 36 | 246 |
| 0.25 | 0.25 | 1 | 26 | 20 | 82 | 22 | 150 |
| 0.25 | 0.25 | 0.5 | 26 | 12 | 44 | 11 | 93 |
| 0.25 | 0.25 | 0.25 | 26 | 15 | 60 | 12 | 113 |

6 wt. % $H_2O$, 175° C.

The reproducibility of this method was also tested in which repeat runs of two different conditions were carried out. The data in Table 13 indicate that this method is highly reproducible.

TABLE 13

| HI (M) | TPPO (M) | TBPO (M) | Run Time (hrs) | Fe | Cr | Ni | Mo | Total |
|---|---|---|---|---|---|---|---|---|
| 0.25 | 0.5 | N/A | 1.5 | 33 | 42 | 165 | 37 | 277 |
| 0.25 | 0.5 | N/A | 1.5 | 52 | 39 | 150 | 35 | 278 |
| 0.25 | N/A | 0.5 | 1.5 | 42 | 60 | 224 | 52 | 378 |
| 0.25 | N/A | 0.5 | 1.5 | 79 | 56 | 219 | 53 | 407 |

6 wt. % $H_2O$, 175° C.

INCORPORATED REFERENCES

The following patents are hereby incorporated by reference in their entirety and for all purposes as if expressly set forth verbatim herein:

U.S. Pat. No. 6,552,221, entitled, "Process Control for Acetic Acid Manufacture", and issued Apr. 22, 2003, to Millennium Petrochemicals, Inc.

U.S. Pat. No. 5,817,869, entitled, "Use of Pentavalent Group VA Oxides in Acetic Acid Processing", and issued Oct. 6, 1998, to Quantum Chemical Corporation.

U.S. Pat. No. 5,932,764, entitled, "Iridium-Catalyzed Carbonylation Process for the Production of a Carboxylic Acid", and issued Aug. 3, 1999, to BP Chemicals Limited.

U.S. Pat. No. 4,909,939, entitled, "Process for solvent extraction using phosphine oxide mixtures", and issued Mar. 20, 1990, to American Cyanamid Company.

In the event of conflict between one or more of the incorporated patents and the present disclosure, the present specification, including definitions, controls.

CLOSING OF THE DETAILED DESCRIPTION

Therefore, the embodiments as disclosed herein are well adapted to attain the ends and advantages mentioned as well as those that are inherent therein. The particular embodiments disclosed above are illustrative only, as such they may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the appended claims. Accordingly, the protection sought herein is as set forth in the claims below.

The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

What is claimed is:

1. A process for producing acetic acid comprising:
   contacting methanol and carbon monoxide in the presence of a liquid reaction medium comprising iodide under carbonylation conditions sufficient to form acetic acid, wherein the liquid reaction medium comprises:
      a carbonylation catalyst selected from the group consisting of rhodium catalysts, iridium catalysts and palladium catalysts;
      1-14 wt. % water; and
      one or more additives at an additive to iodide ratio of 1:1 to 5:1, in-situ generated derivatives of the one or more additives or combinations thereof;
         wherein the one or more additives comprise a compound mixture of tri-n-octylphosphine oxide (TOPO), tri-n-hexylphosphine oxide (THPO), dihexylmonooctylphosphine oxide and dioctylmonohexylphosphine oxide; and
   recovering acetic acid.

2. The process of claim 1, wherein the one or more additives additionally comprises an additive package comprising at least two additive package additives, in-situ generated derivatives of the at least two additive package additives, or combinations thereof, and wherein the at least two additive package additives are independently selected from the group consisting of non-benzoyl containing pentavalent phosphine oxides, compound mixtures of at least four phosphine oxides, and pentavalent aryl or alkaryl phosphine oxides comprising one or more benzoyl groups.

3. The process of claim 2, wherein the pentavalent aryl or alkaryl phosphine oxides comprising one or more benzoyl groups are selected from bis(2,4,6-trimethylbenzoyl) phenyl phosphine oxide (BAPO), (2,4,6-trimethylbenzoyl) diphenyl phosphine oxide (TMDPO) and combinations thereof.

4. The process of claim 2, wherein the non-benzoyl containing pentavalent phosphine oxides are selected from the group consisting of triethyl phosphine oxide, tributyl phosphine oxide, tripentyl phosphine oxide, diphenylmethyl phosphine oxide, triphenyl phosphine oxide and combinations thereof.

5. The process of claim 2, wherein the non-benzoyl containing pentavalent phosphine oxides comprise a phenyl group directly bonded to the phosphorous atom.

6. The process of claim 2, wherein the additive package comprises essentially equal concentrations of each of the at least two additive package additives.

7. The process of claim 1, wherein the reaction medium comprises 1-10 wt. % water.

8. The process of claim 1, wherein the reaction medium comprises a concentration of additive of 0.005-2.0 mol/L.

9. The process of claim 1, wherein the compound mixture comprises from 1-60 wt. % of each phosphine oxide based on the total weight of compound mixture.

10. The process of claim 1, wherein the compound mixture comprises 12-16 wt. % tri-n-octylphosphine oxide (TOPO), from 8-16 wt. % tri-n-hexylphosphine oxide (THPO), from 28-32 wt. % dihexylmonooctylphosphine oxide and from 40-44 wt. % dioctylmonohexylphosphine oxide.

11. The process of claim 1, further comprising introducing a second concentration of the one or more additives into the process downstream of a reaction zone.

12. The process of claim 11, further comprising adjusting the second concentration in response to a downstream iodide content.

13. The process of claim 11, wherein the second concentration comprises a molar ratio of additive to iodide of 2.5:1 to 3.5:1.

14. The process of claim 1, wherein the one or more additives comprises a non-benzoyl containing pentavalent phosphine oxide and the carbonylation catalyst comprises iridium catalysts.

* * * * *

UNITED STATES PATENT AND TRADEMARK OFFICE
CERTIFICATE OF CORRECTION

| | | |
|---|---|---|
| PATENT NO. | : 10,067,113 B2 | Page 1 of 1 |
| APPLICATION NO. | : 14/630054 | |
| DATED | : September 4, 2018 | |
| INVENTOR(S) | : Hallinan et al. | |

It is certified that error appears in the above-identified patent and that said Letters Patent is hereby corrected as shown below:

In the Specification

In Column 6, Line 11, after "2,4,6-trimethylbenzoyl" insert -- ) --
In Column 9, Line 9, after "of" before "reaction" insert -- the --
In Column 12, Line 34, delete "obverserved" and insert -- observed --
In Column 13, Line 12, delete "0.51M," and insert -- 0.5M, --
In Column 13, Line 32, delete "a" and insert -- an --, therefor
In Column 19, Line 32, delete "light-ends column 140." and insert -- heavy-ends column 150. --
In Column 26, Line 23, after "At" insert -- the --

Signed and Sealed this
Eighteenth Day of January, 2022

Drew Hirshfeld
*Performing the Functions and Duties of the*
*Under Secretary of Commerce for Intellectual Property and*
*Director of the United States Patent and Trademark Office*